US007101979B1

(12) United States Patent
Boehm et al.

(10) Patent No.: US 7,101,979 B1
(45) Date of Patent: Sep. 5, 2006

(54) ANTIBODIES TO ANTIANGIOGENIC COMPOSITIONS AND METHODS

(75) Inventors: Thomas Boehm, Brookline, MA (US); Michael S. O'Reilly, Winchester, MA (US); M. Judah Folkman, Brookline, MA (US)

(73) Assignee: The Children's Medical Center Corporation, Boston, MA (US)

( * ) Notice: Subject to any disclaimer, the term of this patent is extended or adjusted under 35 U.S.C. 154(b) by 409 days.

(21) Appl. No.: 10/142,707

(22) Filed: May 9, 2002

Related U.S. Application Data

(63) Continuation of application No. 08/977,188, filed on Nov. 24, 1997, now abandoned, which is a continuation-in-part of application No. 08/740,168, filed on Oct. 22, 1996, now Pat. No. 5,854,205.

(60) Provisional application No. 60/026,263, filed on Sep. 17, 1996, provisional application No. 60/023,070, filed on Aug. 2, 1996, provisional application No. 60/005,835, filed on Oct. 23, 1995.

(51) Int. Cl.
A61K 39/395 (2006.01)
(52) U.S. Cl. ............... 530/388.8; 530/324; 530/387.7; 530/387.9; 530/388.1; 435/810; 435/325; 435/326; 435/331; 435/344.1; 435/330
(58) Field of Classification Search ............... 530/324, 530/387.7, 387.9, 388.1, 388.8; 435/810, 435/325, 326, 331, 344.1, 344, 330
See application file for complete search history.

(56) References Cited

U.S. PATENT DOCUMENTS

| 5,643,783 A | 7/1997 | Olsen et al. |
| 6,080,728 A | 6/2000 | Mixson |

FOREIGN PATENT DOCUMENTS

| JP | 58036391 | 3/1983 |
| WO | WO 91/10424 | 7/1991 |
| WO | WO 93/16716 | 9/1993 |
| WO | WO 95/25543 | 9/1995 |
| WO | WO 95/29242 | 11/1995 |

OTHER PUBLICATIONS

Author: Title: Chapter 12: Vectors for Gene Therapy Publ: *Current Protocols in Human Genetics* Vol/Iss: Pages: Date: 1997.
Author: Abe, N. et al. Title: Identification of a Novel Collagen Chain Represented by Extensive Interruptions in the Triple-Helical Region Publ: *Biochemical and Biophysical Research Communications* vol./Iss: 196 (2) pp.: 576-582 Date: Oct. 29, 1993.
Author: Algire, G.H. et al. Title: Vascular reactions of normal and milignant tumors in vivo. I. Vascular reactions of mice to wounds and to normal and neoplastic transplants Publ: *Journal of the National Cancer Institute* vol./Iss: 6 pp.: 73-85 Date: Aug. 1945.

Author: Angiolillo, A. et al. Title: Human Interferon-inducible Protein 10 is a Protent Inhibitor of Angiogenesis in Vivo. Publ: *The Journal of Experimental Medicine* vol./Iss: 182 pp.: 155-162 Date: Jul. 1995.
Author: Boussif, O. et al. Title: A versatile vector for gene and oligonuclotide transfer into cells in culture and in vivo Publ: *Proc. Natl. Acad. Sci. USA* vol./Iss: 92 pp.: 7297-7301 Date:Aug. 1995.
Author: Brem, H. et al. Title: Interstitial chemotherapy with drug polymer inplmants for the treatment of recurrent gliomas. Publ: *Journal of Neurosurgery* vol./Iss: 74 pp.: 441-446 Date: Mar. 1, 1991.
Author: Brockway, W. J. et al. Title: Measurement of the Binding of Antifibrinolytic Amino Acids to Various Plasminogens Publ: *Archives of Biochemistry and Biophysics* vol./Iss: 151 pp.: 194-199 Date: Apr. 18, 1972.
Author: Browne Title: Expression of Recombinant Human Plasminogen and Aglycoplasmingoen in HeLa cells Publ: *Fibinolysis* vol./Iss: 5 pp.: 257-260 Date: Apr. 13, 1991.
Author: Calos, Michael P. Title: The potential of extrachromosomal replicating vectors for gene therapy Publ: *TIG* vol./Iss: 12 (11) pp.: 463-466 Date: Nov. 1996.
Author: Campbell, Alisa M. Title: General Properties and applications of monoclonal antibodies Publ: *Monoclonal Antibody Technology* Vol/Iss: pp.: 1-30 Date: 1984.
Author: Cao, Y. et al. Title: gro-B, a-C-X-C- Chemokine, is an Anglogenesis inhibitor that Suppresses the Growth of Lewis Lung Carnioma in Mice Publ: *Journal of Experimental Medicine* vol./Iss: 182 pp.: 2069-2077 Date: Dec. 1, 1995
Author: Chen, C. et al. Title:A Strategy to Discover Circulating Angiogensis Inhibitors Generated by Human Tumors Publ: *Cancer Research* vol./Iss: 55 pp.: 4230-4233 Date: Oct. 1, 1995.
Author: Chen, P. et al. Title: Genetic Mechanisms of Tumor Suppression by the Human p53 Gene Publ: *Science* vol./Iss: 250 pp.: 1576-1579 Date: Dec. 1990.
Author: Cheng, Pi-Wan Title: Receptor Ligand-Facilitated Gene Transfer: Enhancement of Liposome-Mediated Gene Transfer and Expression by Transferrin Publ: *Human Gene Therapy* vol./Iss: 7 pp.: 7 Date: Feb. 10, 1996.
Author: Clapp, C. et al. Title: The 16-kilodation N-terminal Fragment Of Human Prolactin Is A Protent Inhibitor Of Angiogenesis Publ: *Endocrinology* vol./Iss: 133 pp.: 1292-1299 Date: Mar. 1, 1993.
Author: Cleary, S. et al. Title: Purification and Characterization of Tissue Plasminogen Activator Kringle-³ Domain Expressed in *Esherica coli* Publ: *Biochemistry* vol./Iss: 28 pp.: 1884-1891 Date: 1989.
Author: Dameron, K.M. et al. Title: Control of Angiogenesis in Fibroblasts by p53 Regulation of Thrombospondin-1 Publ: *Science* vol./Iss: 265 pp.: 1582-1584 Date: Sep. 9, 1994.

(Continued)

*Primary Examiner*—Sheela J. Huff
(74) *Attorney, Agent, or Firm*—Kilpatrick Stockton LLP

(57) ABSTRACT

Antibody to endostatin protein that is an inhibitor of endothelial cell proliferation, capable of inhibiting angiogenesis and causing tumor regression, that is approximately 18 kDa as determined by non-reduced gel electrophoresis, and approximately 20 kDa as determined by reduced gel electrophoresis and corresponds to a C-terminal fragment of collagen type XVIII, and methods of detecting and treating angiogenesis-related disease therewith.

28 Claims, 18 Drawing Sheets

OTHER PUBLICATIONS

Author: Dardik, R. et al Title: The structure of enothelial cell thrombospondin—Characterization of the heparin-binding domains Publ: *Eur J Biochem* vol./Iss: 168 (2) pp.: 347-355 Date: Oct. 15, 1987.

Author: Debs, R.J. et al. Title: Regulation of Gene Expression in Vivo by Liposome-mediated Delivery of a Purified Transcription Factor Publ: *The Journal of Biological Chemistry* vol./Iss: 265 (18) pp.: 10189-10192 Date: Jun. 25, 1990.

Author: Dixit, V.M. et al. Title: A monoclonal antibody against human thrombospondin inhibits platelet aggregation Publ: *Proc. Natl. Acad. Sci. USA* vol./Iss: 82 pp.: 3472-3476 Date: May 1985.

Author: Fan et al. Title: Controlling the vasculature: angiogensis, anti-angiogensis and vascular targeting of gene therapy Publ: *Trends in Pharmacolgical Sciences* vol./Iss: 16 pp.: 57-66 Date: Feb. 1995.

Author: Fidler et al. Title: The Implications of Angiogensis for the Biology and Therapy of Cancer Metastasis Publ: *Cell* vol./Iss: 79(2) pp.: 185-188 Date: Oct. 21, 1994.

Author: Folkman, J. Title: Tumor angiogensis and tissue factor Publ: *Nature Medicine* vol./Iss: 2 pp.: 167-168 Date: Feb. 1, 1996.

Author: Folkman, J. Title: What is the Evidence that Tumors are Angiogensis Dependent? Publ: *Journal of the National Cancer Institute* vol./Iss: 82 pp.: 4-6 Date:Jan. 3, 1990.

Author: Folkman, J. Title: Angiogenesis in cancer, vascular, rheumatoid and other disease Publ: *Nature Medicine* vol./Iss: 1(1) pp.: 27-31 Date: Nov. 1, 1995.

Author: Folkman, J. Title: Angiogenesis and Its Inhibitors Publ: *Important Advances in Oncology* Vol/Iss: pp.: 42-62 Date: 1985.

Author: Folkman, J. Title: Tumor Angiogenesis: Therapeutic Implications Publ: *New England Journal of Medicine* vol./Iss: 285(12) pp.: 1182-1186 Date: Nov. 18, 1971.

Author: Folkman, J. et al. Title: Long-term culture of capillary endothelial cells Publ: *Proceedings of the National Academy of Science USA* vol./Iss: 76 pp.: 5217-5221 Date: Oct. 1, 1979.

Author: Folkman, J. et al Title: Induction of angiogensis during the transition from hyperplasia to neoplasia Publ: *Nature* vol./Iss: 339 pp.: 58-61 Date: May 4, 1989.

Author: Folkman, J. et al. Title: Tumor Behavior In Isolated Perfused Oragans in vitro Growth and Metastases of Biopsy Materials in Rabbit Thyroid and Canine Intestinal Segment Publ: *Annals of Surgery* vol./Iss: 164(3) pp.: 491-502 Date: Sep. 1, 1966.

Author: Fujiwara T. et al. Title: Induction of Chemosensitivity in Human Lung Cancer Cells in Vivo by Adenovirus-mediated Transfer of the Wild-Type *p53* Gene Publ: *Cancer Research* vol./Iss: 54 pp.: 2287-2291 Date: May 1, 1994.

Author: Gavrieli, Y. et al. Title: Identification of Programmed Cell Death in Situ via Specific Labelling of Nuclear DNA Fragmentation Publ: *Journal of Cell Biology* vol./Iss: 119 pp.: 493-501 Date: 1992.

Author: Gimbrone, M.A. et al. Title: Tumor growth and neovascularization: An experimental model using the rabbit comea Publ: *Journal of the National Cancer Institute* vol./Iss: 52(2) pp.: 413-427 Date: Feb. 1974.

Author: Gimbrone, M.A. et al. Title: Tumor dormancy in vivo by Prevention of Neovascularization Publ: *Journal of Experimental Medicine* vol./Iss: 136 pp.: 261-276 Date: 1972.

Author: Goldman, C.K. et al. Title: In vitro and in vivo gene delivery mediated by a synthetic polycationic amino polymer Publ: *Nature Brochure* vol./Iss: 15 pp.: 462-466 Date: May 1997.

Author: Good, DJ. et al. Title: A tumor suppressor-dependent inhibitor of angiogensis is immunologically and functionally indistinguishable from a fragment of therbospondin Publ: *Proceedings of the National Academy of Science USA* vol./Iss: 87 pp.: 6624-6628 Date: Sep. 1990.

Author: Grant, D.S. et al. Title: Scatter factor induces blood vessel formation in vivo Publ: *Proceedings of the National Academy of Science USA* vol./Iss: 99 pp.: 1937-1941 Date: Mar. 1993.

Author: Grant, D.S. et al. Title: Two Different Laminin Domains Mediate the Differentiation of Human Endothelial Cells into Capillary-like Structures in Vitro Publ: *Cell* vol./Iss: 58 pp.: 933-943 Date: Sep. 8, 1989.

Author: Gross, J.L. et al. Title: Modulation of Solid Tumor Growth in vivo by bFGF (Abstract only) Publ: *Proceedings of the American Association of Cancer Research* vol./Iss: 31 pp.: 79 Date: Mar. 1990.

Author: Gross, J.L. et al. Title: Increased capillary enothlial cell protease activity in response to angiogenic stimuli in vitro Publ: *Proceedings of the National Academy of Science USA* vol./Iss: 80 pp.: 2623-2627 Date: May 1983.

Author: Gunzler, W.A. et al. Title: The Primary Structure of High Molecular Mass Urokinase from Human Urine Publ: *Hoppe-Seyler's Z. Physiol. Chem.* vol./Iss: 363 pp.: 1155-1165 Date: Oct. 1982.

Author: Gupta, S. et al. Title: A potent inhibitor of endothelial cell protiferation is generated by proteolytic cleavave of the chemokine platelet factor 4 Publ: *Proceedings of the National Academy of Science USA* vol./Iss: 92 pp.: 7799-7803 Date: Aug. 1995.

Author: Hawkins, Michael J, M.D. Title: Clincal trials of antiangiogenic agents Publ: *Current Journal of Pathology* vol./Iss: 120 pp.: 327-332 Date: Nov. 15, 1991.

Author: Holgren, L. et al. Title: Dormancy of micrometastases: Balanced proliferation and apoptosis in the presence of anglogenesis suppression Publ: *Nature Medicine* vol./Iss: 1 (2) pp.: 149-153 Date: Feb. 1995.

Author: Homandberg, G.A. et al. Title: Heparin-binding Fragments of Fibronectin are Potent Inhibitors of Endothelial Cell Growth Publ: *American Journal of Pathology* vol./Iss: 120 pp.: 327-332 Date: Sep. 1985.

Author: Hori, A. et al. Title: Suppression of Solid Tumor Growth by Immunoneutralizing Monoclonal Antibody Against Human Basic Fibroblasts Growth Factor Publ: *Cancer Research* vol./Iss: 51 pp.: 6180-6184 Date: Nov. 15, 1991.

Author: Ingber, D. et al. Title: Synthetic analogues of fumagillin that inhibit angiogenesis and suports tumor growth Publ: *Nature* vol./Iss: 348 pp.: 555-557 Date: Dec. 6, 1990.

Author: Johnson, J. et al. Title: Surfactant Protein B: Disulfide Bridges, Structural Properties, and Kringle Similatities Publ: *Biochemsty* vol./Iss: 30 (28) pp.: 6917-6921 Date: 1991.

Author: Kandel, J. et al. Title: Neovascularization is Associated with a Switch to the Export of bFGF in the Multistep Development of Fibrosarcoma Publ: *Cell* vol./Iss: 66 pp.: 1095-1104 Date: Sep. 20, 1991.

Author: Kim, K.J. et al. Title: Inhibition of vascular endothelial growth factor-induced angiogensisn suppresss tumor growth in Vivo Publ: *Nature* vol./Iss: 362 pp.:841-844 Date: Apr. 29, 1993.

Author: King, Ralph P. Jr. Title: Novel Cancer Approach From Noted Scientist Hits Stumbling Block Publ: *Wall Street Journal* Vol/Iss: pp.: A1-A8 Date: Nov. 12, 1999.

Author: Kivirikko, S. et al. Title: Primary Structure of the α1 Chain of Human Type XV Collagen and Exon-Intron Organization in the 3' Region of the Corresponding Gene Publ: *Journal of Biological Chemistry* vol./Iss: 269 pp.: 4773-4779. Date: Feb. 18, 1994.

Author: Knighton, D. et al. Title: Avascular and Vascular Phases of Tumour Growth in the Chick Embyo Publ: *British Journal of Cancer* vol./Iss: 35 pp.: 347-356 Date: 1977.

Author: Kosfeld, M.D. et al. Title: Identification of a New Cell Adhesion Motif in Two Homologous Peptides from the COOH-terminal Cell Binding Domain on Human Thrombospondin Publ: *The Journal of Biological Chemistry* vol./Iss: 268 (12) pp.: 8808-8814 Date: 1993.

Author: Lerch et al. Title: Localization of Individual Lysine-Binding Regions in Human Plasminogen and Investigations on Their Complex-Forming Properties Publ: *European Journal of Biochemistry* vol./Iss: 107(1) pp.: 7-13 Date: 1980.

Author: Lesoon-Wood, L.A. et al. Title: Systemic Gene with p53 Reduces Growth and Metastases of a Malignant Human Breat Tumor in Nude Mice Publ: *Human Gene Therapy* vol./Iss: 6 pp.: 395-405 Date: Apr. 1995.

Author: Lien, W. et al. Title: The blood supply of experimental liver metastases. II. A Microcirculatory study of the normal and tumor vessels of the liver with the use of perfused silicone rubber Publ: *Surgery* vol./Iss: 68 (2) pp.: 334-340 Date: Aug. 1970.

Author: Lokker, N.A. et al. Title: Mutational analysis and molecular modeling of the N-terminal kringle-containing domain of hepatocyte growth factor identifies amino acid side chains important for interaction with the c-met receptor Publ: *Protein Engineering* vol./Iss: 7(7) pp.: 895-903 Date:Jul. 1994.

Author: Maione, T.E. et al. Title: Inhibition of Angiogensis by Recombinant Human Platlet Factor-4 and Related Peptides Publ: *Science* vol./Iss: 247 pp.: 77-79 Date: Jan. 5, 1990.

Author: Maione, T.E. et al. Title: Inhibition of Tumor Growth in Mice by an Analogue of Platelet Factor 4 That Lacks Affinity for Heparin and Retains Angiostatic Activity Publ: *Cancer Research* vol./Iss: 51 pp.: 2077-2083 Date: Apr. 15, 1991.

Author: Marshall, Eliot Title: Gene Therapy's Growing Pains Publ: *Science* vol./Iss: 269 pp.: 1050-1055 Date: Aug. 25, 1995.

Author: Marti, D. et al. Title: Expression, purification and characterization of the recombinant kringle 2 and kringle 3 domains of human plasminogen and analysis of their binding affinity for w-aminocarboxylic acids Publ: *European Journal of Biochemistry* vol./Iss: 219 pp.: 455-462 Date: 1994.

Author: McLean, J.W. et al. Title: cDNA sequence of human apoliprotein(1) is homologous to plasminogen Publ: *Nature* vol./Iss: 330 pp.: 132-137 Date: Nov/ 12, 1987.

Author: Menhart, N. et al. Title: Construction, Expression and Purification of Recombinant Kringle 1 of Human Plasminogen and Analysis of Its Interaction with w-Amino Acids Publ: *Biochemistry* vol./Iss: 30 pp.: 1948-1957 Date: 1991.

Author: Millauer, B. et al. Title: Glioblastoma growth inhibited in vivo by a dominant-negative Flk-1 mutant Publ: *Nature* vol./Iss: 367 pp.: 576-579 Date: Feb. 10, 1994.

Author: Moses, M.A. et al. Title: Identification of an Inhibitor of Neovasculatization from Cartilage Publ: *Science* vol./Iss: 248 Pages: Date: Jun. 15, 1990.

Author: Muragaki, Y. et al. Title: Mouse col18a1 is expressed in a tissue-specific manner as three alternative variants and is localized in basement membrane zones Publ: *Proceedingss of the National Academy of Science USA* vol./Iss: 92 pp.: 8763-8767 Date: Sep. 1995.

Author: Nelson, J. et al. Title: Murine Epidemal Growth Factor (egf) Fragment (33-42) Inhibits Both Egf- And Laminin-dependent Endothlial Cell Motility And Angiogensis Publ: *Cancer Research* vol./Iss: 55 pp.: 3772-3776 Date: Sep. 1, 1995.

Author: Nguyen et al. Title: Elevated Levls of the Angiogenic Peptide Basic Fiberoblast Gorwth Factor in Urine of Patients with Wide Spectrum of Cancers Publ: *Journal of the National Cancer Institute* vol./Iss: 86 (5) pp.: 356-361 Date: 1994.

Author: Nguyen, M. et al. Title: Quantitation of Angiogensis and Antiangiogensis in the Chick Embryo Chorioallantoic Membrane Publ: *Microvascular Research* vol./Iss: 47 pp.: 31-40 Date: 1994.

Author: O'Reilly et al. Title: Endogenous Inhibitors of Angiogenesis (Abstract only) Publ: *Proceedings of the American Association of Cancer Research* vol./Iss: 37 pp.: 669 Date: Mar. 1996.

Author: O'Reilly et al. Title: Angiostatin induces and sustains domancy of human primary tumors in mice Publ: *Nature Medicine* vol./Iss: 2(6) pp.: 689-692 Date: Jun. 1996.

Author: O'Reilly et al. Title: The Suppression of Tumor Metastases by a Primary Tumor Publ: *79th Annual Clinical Congress—San Francisco—Surgical Forum* vol./Iss: XLIV pp.: 474-476 Date: 1993.

Author: O'Reilly et al. Title: Angiostatin: A Novel Angiogensis Inhibitor that Mediates the Suppression of Metastases by a Lewis Lung Carcinoma Publ: *Cell* vol./Iss: 79 pp.: 315-328 Date: Oct. 21, 1994.

Author: O'Reilly et al. Title: Angiostatin: A Circulating Endothelial Cell Inhibitor That Suppreses Angiogenesis and Tumor Growth Publ: *Cold Spring Habor Symposia on Quantitative Biology* vol./Iss: LIX pp.: 471-482 Date: 1994.

Author: O'Reilly et al. Title: Endostatin: An Endogenous Inhibitor of Angiogenesis and Tumor Growth Publ: *Cell* vol./Iss: 88 pp.: 277-285 Date: Jan. 24, 1997.

Author: Obeso, J. et al. Title: Methods in Laboratory Investigation/A Hemangioendothelioma-Derived Cell Line: Its Use as a Model for the Study of Endothelial Cell Biology Publ: *Laboratory Investigation* vol./Iss: 63(2) pp.: 259-269 Date: 1990.

Author: Oh, S.P. Title: Cloning of cDNA and Genomic DNA Encoding Human Type VIII Collagen and Localization of the a-1 (XVIII) Collagen Gene to Mouse Chromosome 10 and Human Chromosome 21 Publ: *Genomics* vol./Iss: 19 pp.: 494-499 Date: 1994.

Author: Oh, S.P. et al. Title: Isolation and sequencing of cDNAs for proteins with multiple domains of Gly-Xaa-Yaa repeats identify a distinct family of collagenous proteins Publ: *Proceedings of the National Academy of Science USA* vol./Iss: 91 pp.: 4229-4233 Date: May 1994.

Author: Parangi, S. et al. Title: Antiangiogenic therapy of transgenic mice impairs de novo tumor growth Publ: *Proceedings of the National Academy of Science USA* vol./Iss: 93 pp.: 2002-2007 Date: Mar. 1996.

Author: Park et al. Title: Development of liposome- and anti-HER2 immunoliposomeplasmid complexes for efficient and selective gene therapy Publ: *Proceedings of the American Association for Cancer Research* vol./Iss: 38 pp.: 342 Date: Mar. 1997.

Author: Pasqualini, R. et al. Title: αv Integrins as receptors for tumor targeting by circulating ligands Publ: *Nature Blotechnology* vol./Iss: 15 pp.: 542-546 Date: Jun. 1997.

Author: Pasqualini, et al. Title: Organ targeting in vivo using phage display peptide libraries Publ: *Nature* vol./Iss: 380 pp.: 364-166 Date: Mar. 28, 1996.

Author: Passaniti, A. et al. Title: Methods in Laboratory Investigation/A Simple, Quantiative Method for Assessing Angiogenesis and Antiangiogenic Agents Using Reconstituted Basement Membrane, Heparin, and Fibroblast Growth Factor Publ: *Laboratory: Investigation* vol./Iss: 67(4) pp.: 519-528 Date: 1992.

Author: Ponting et al. Title: Plastminogen: A structural review Publ: *Blood Coagulation and Fibrinoylsis* vol./Iss: 3 pp.: 605-614 Date: 1992.

Author: Powell, J.R. et al. Title: Amino Acid Sequence Analysis of teh Asparagine-288 Region of the Carbohydrate Variants of Human Plasminogen Publ: *Biochemistry* vol./Iss: 22 pp.: 923-927 Date: 1983.

Author: Rastinesad, F. et al. Title: Regulation of the Activity Of A New Inhibitor Of Angiogenesis By A Cancer Suppressor Gene Publ: *Cell* vol./Iss: 56 pp.: 345-355 Date: Feb. 10, 1989.

Author: Rehn et al. Title: Primary structure of the alpha 1 chain of mouse type XVIII collagen, partial structure of the corresponding gene, and comparison of the alpha 1 (XVIII) chain with its homologue, the alpha 1 (XV) collagen gene (abstract only) Publ: *Journal of Biological Chemistry* vol./Iss: 269(19) pp.: 13929-13935 Date: 1994.

Author: Rehn, M. et al. Title: α1 (XVIII), a collagen chain with frequent interruptions in the collagenous sequence, a distinct tissue distribution, and homology with type XV collagen Publ: *Proceedings of the National Academy of Science, USA* vol./Iss: 91 pp.: 4234-4238 Date: May 1994.

Author: Rehn, M. et al. Title: Identification of Three N-terminal Ends of Type XViii Collagen Chains And Tissue-specific Differences in The Expression Of The Corresponding Transcripts Publ: *Journal of Biological Chemistry* vol./Iss: 270 pp.: 4705-4711 Date: Mar. 3, 1995.

Author: Robbins, K.C. Title: Fibrinolysis: The Plasminogen-plasmin enzyme system Publ: *Hemostasis and Thrombosis, Basic Principles and Practice, 2nd Edition* Vol/Iss: pp.: 340-357 Date: 1995.

Author: Sage, E.H. et al. Title: Inhibition of Endothelial Cell Proliferation by SPARC is Mediated through a $Ca^{2+}$-Binding EF-Hand Sequence Publ: *Journal of Cellular Biochemistry* vol./Iss: 57 pp.: 127-140 Date: 1995.

Author: Saiki et al. Title: Inhibition of Tumor Ahgiogenesis by a Synthetic Cell-adhesive Polypeptide Containing the Arg-Gly-Asp (RGD) Sequence of Fibronectin, Poly(RGD) Publ: *Jpn. J. Cancer Research* vol./Iss: 81 pp.: 668-675 Date: 1990.

Author: Sakamoto, N. et al. Title: Inhibition of Angiogenesis And Tumor Growth By A Synthetic Laminin Peptide. Cdpgyigsr-nh2 Publ: *Cancer Research* vol./Iss: 51 pp.: 903-906 Date: Feb. 1, 1991.

Author: Sambrook, J. et al. Title: Expression of Cloned Genes in Escherichia coli Publ: *Molecular Cloning Second Edition* Vol/Iss: pp.: 17.37-37.41 Date: 1989.

Author: Schaller, J. et al. Title: Structural Aspects of the Plasminogen of Various Species Publ: *Enzyme* vol./Iss: 40 pp.: 63-69 Date: 1988.

Author: Sheikh et al. Title: Overexpression of p21WAF1/CIP1 induces frowth arrest, giant cell formation and apoptosis in human breast carcinome cell lines Publ: *Oncogene* vol./Iss: 11 pp.: 1899-1905 Date: 1995.

Author: Shi, G. et al. Title: Kringle Domains and Plasmin Denaturation Publ: *Biochemistry Biophysiology Research Communications* vol./Iss: 178(1) pp.: 360-368 Date: Jul. 15, 1991.

Author: Sottrup-Jensen, L. et al. Title: The Primary Structure of Human Plasminogen Isolation of Two-Lysine-Binding Fragments and One "Mini-"PLasminogen (MW. 38,000) by Elaslasr-Catalyzed-Specific Limited Proteolysis Publ: *Progress in Chemical Fibrinolysis and Thrombolysis* vol./Iss: 3 pp.: 191-209 Date: 1978.

Author: Srivastava, A. et al. Title: The Prognostic Significance of Tumorvascularity in Intermediate-Thickness (0.76-4.0 mm Thick) Skin Metanoma Publ: *American Journal of Pathology* vol./Iss: 133 (2) pp.: 419-424 Date: Nov. 1988.

Author: Streiter, R.M. et al. Title: Interferonγ-Inducible Protein 10 (IP-10), A Member of the C-X-C Chemokine Family, is an Inhibitor of Angiogenesis Publ: *Biochemistry Biophysiology Research Communications* vol./Iss: 210 pp.: 51-57 Date: May 5, 1995.

Author: Studier, W.F. et al. Title: Use of T7 RNA Polymerase To Direct Epxression Of Cloned Genes Publ: *Methods of Enzymology* vol./Iss: 185 pp.: 60-89 Date: 1990.

Author: Tanaka, T. et al. Title: Viral vector-mediated transductions of a modified platelet factor 3 cDNA inhibits angiogensis and tumor growth Publ: *Nature Medcinie* vol./Iss: 3 pp.: 437-442 Date: Apr. 1997.

Author: Teicher, B.A. et al. Title: Potentiation of Cytotoxic Cancer Therapies by TNP-470 Alone and with Other Antiangiogenic Agents Publ: *International Journal of Cancer* vol./Iss: 57 (6) pp.: 920-925 Date: 1994.

Author: Tolsma, S.S. et al. Title: Peptides Derived From Two Separate Domains Of The Matrix Protein Thrombospondin-1 Have Antiangiogenic Activity Publ: *Journal of Cell Biology* vol./Iss: 122 pp.: 497-511 Date: Jul. 1993.

Author: Van Meir, E. et al. Title: Release of an inhibitor of angiogensis upon induction of wild type p53 expression in glioblastoma cells Publ: *Nature Genetics* vol./Iss: 8 pp.: 171-176 Date: Oct. 1994.

Author: Voest, E.E. et al. Title: Inhibition of Angiogensis in Vivo by Interleukin 12 Publ: *Journal of the national Cancer Institute* vol./Iss: 87 pp.: 581-586 Date: Apr. 19, 1995.

Author: Walz, D.A. et al. Title: Amino acid sequence of human prothrombin fragments 1 and 2 Publ: *Proceedings of the National Academy of Science* vol./Iss: 74 pp.: 1969-1973 Date: May 1977.

Author: Weidner, N. et al., Title: Tumor angiogensis: A New Significant and Independent Prognostic Indicator in Early-Stage Breast Carcinoma Publ: *Journal of the National Cancer Institute* vol./Iss: 84 pp.: 1875-1887 Date: Dec. 16, 1992.

Author: Weidner, N. et al. Title: Tumor Angiogenesis Correlates with Metastasis in Invasive Prostate Carcinoma Publ: *American Journal of Pathology* vol./Iss: 143 (2) pp.: 401-409 Date: Aug. 1993.

Author: Weidner, N. et al. Title: Tumor Angiogenesis and Metastasis-Correlation in Invasive Breast Carcinoma Publ: *New England Journal of Medicine* vol./Iss: 324 (1) pp.: 1-8 Date: Jan. 3, 1991.

Author: Weinstat-Saslow, D.L. et al. Title: Transdection of Thrombaspondin 1 Complementary DNA into a Human Breast Carcinoma Cell Line Reduces Primary Tumor Growth, Metastatic Potential, and Angiongenesis Publ: *Cancer Research* vol./Iss: 54 pp.: 6504-6511 Date: 1994.

Author: Werkmeister et al. Title: Characterisation of a monoclonal antibody angainst native human type 1 collagen Publ: *European Journal of Biochemsitry* vol./Iss: 187 pp.: 439-443 Date: 1990.

Author: Wiman, B. et al. Title: On the Specific Interaction Between the Lysine-Binding SItes in Plasmin and Complementary Sites in a2-Antiplasmin and Fibinogen Publ: *Biochimica et Biophysica Acta.* vol./Iss: 579 pp.: 142-154 Date: 1979.

Author: Xu, M. et al. Title: In Vivo Gene Therapy with a Cationic Polymer Markedly Enhances the Antitumor Activity of Antiangiogenic Genes Publ: *Molecular Genetics and Metabolism* vol./Iss: 64 pp.: 1-5 Date: 1998.

Author: Xu, M. et al. Title: Gene Therapy with P53 and a Fragment of Thrombospondin I Inhibits Human Breal Cancer in Vivo Publ: *Molecular Genetics and Metabolism* vol./Iss: 63 pp.: 103-109 Date: 1998.

Author: Xu, M. et al. Title: Parenteral Gene Therapy with p53 Inhibits Human Breat Tumors in vivo Through a Bystander Mechanism Without Evidence of Toxicity Publ: *Human Gene Therapy* vol./Iss: 8 pp.:177-185 Date: Jan. 20, 1997.

Author: Yoshimura, T. et al. Title: Cloning, Sequencing, and Expression of Human Macrophage Stimulatnig Protein (MSP, MSTI) Confirms MSP as a Member of the Family of Kringle Proteins and Locates the MSP Gene on Chromosome 3 Publ: *The Journal of Biological Chemistry* vol./Iss: 268 (21) pp.: 15461-15468 Date: Jul. 25, 1993.

Author: Zabrenetzky, V. et al. Title: Expression of the Extracellular Matrix Molecule Thrombospondin Inversely Correlates with Malignant Progression in Melanoma, Lung and Breast Carcinoma Cell Publ: *Int. J. Cancer* vol./Iss: 59 pp.: 191-195 Date: 1994.

Author: Zhu, N. et l. Title: Systemic Gene Expression After Intravenous DNA Delivery into Adult Mice Publ: *Science* vol./Iss: 261 pp.: 209-211 Date: Jul. 9, 1993.

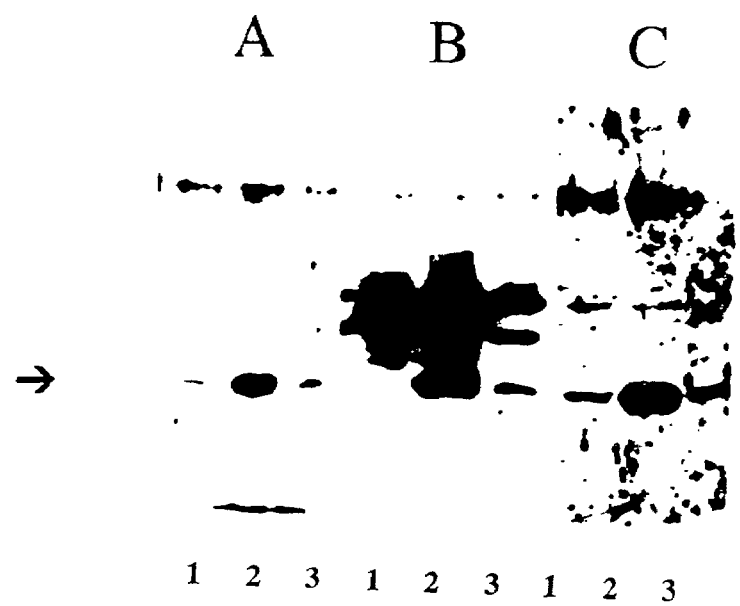
Figure 16.A
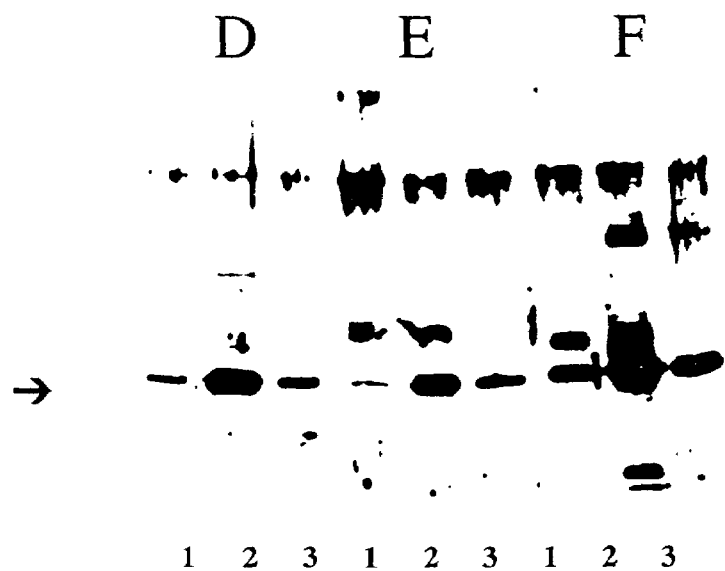
Figure 16.B

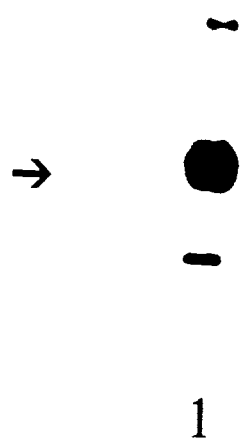
Figure 15.A
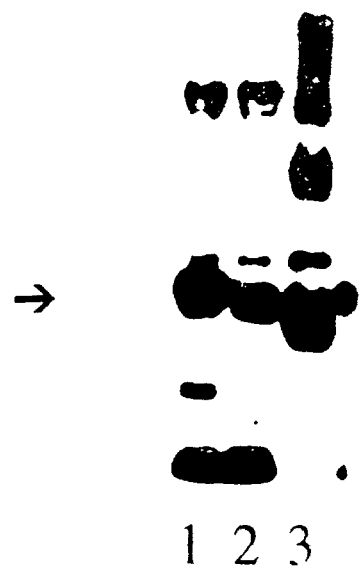
Figure 15.B

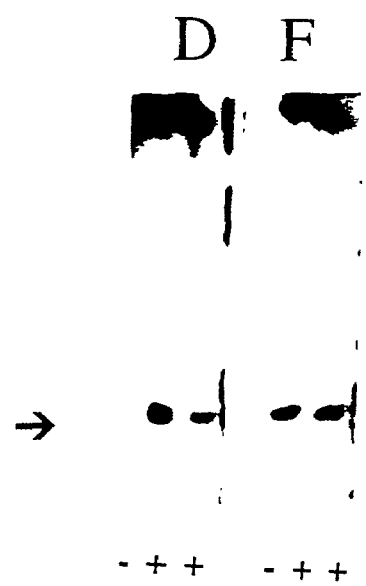
Figure 17.A
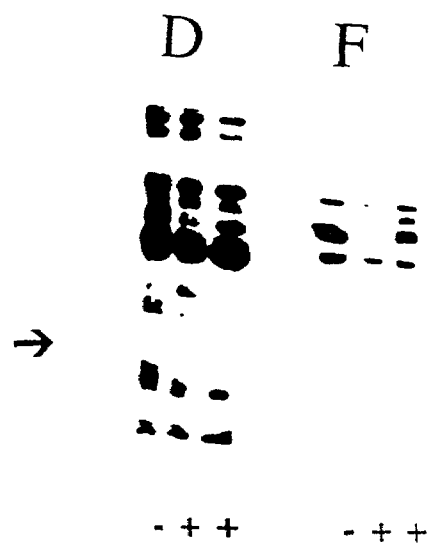
Figure 17.B

US 7,101,979 B1

ANTIBODIES TO ANTIANGIOGENIC COMPOSITIONS AND METHODS

CROSS REFERENCE TO PRIOR RELATED CASES

This application is a continuation of U.S. patent application Ser. No. 08/977,188 filed Nov. 24, 1997, now abandoned, which is a continuation-in-part of U.S. patent application Ser. No. 08/740,168 filed Oct. 22, 1996, and issued as U.S. Pat. No. 5,854,205, which claims priority to provisional application Ser. No. 60/005,835 filed Oct. 23, 1995; provisional application Ser. No. 60/023,070 filed Aug. 2, 1996; and provisional application Ser. No. 60/026,263 filed Sep. 17, 1996. Each of the above-referenced applications is incorporated herein in its entirety.

This invention may have been made in part by funds from NIH grants RO1-CA64481 and PO1-CA45548. The U.S. Government may have certain rights in this invention.

TECHNICAL FIELD

This application relates to a novel inhibitor of angiogenesis, termed endostatin protein, useful for treating angiogenesis-related diseases, such as angiogenesis-dependent cancer. The invention further relates to a novel composition and method for curing angiogenesis-dependent cancer. In addition, the present invention relates to diagnostic assays and kits for endostatin protein measurement, to histochemical kits for localization of endostatin protein, to molecular probes to monitor endostatin protein biosynthesis, to antibodies that are specific for the endostatin protein or peptides, to the development of peptide agonists and antagonists to the endostatin protein receptor, and to cytotoxic agents linked to endostatin protein or peptides.

BACKGROUND OF THE INVENTION

Several lines of direct evidence now suggest that angiogenesis is essential for the growth and persistence of solid tumors and their metastases (Folkman, 1989; Hori et al., 1991; Kim et al., 1993; Millauer et al., 1994). To stimulate angiogenesis, tumors upregulate their production of a variety of angiogenic factors, including the fibroblast growth factors (FGF and BFGF) (Kandel et al., 1991) and vascular endothelial cell growth factor/vascular permeability factor (VEGF/VPF). However, many malignant tumors also generate inhibitors of angiogenesis, including angiostatin protein and thrombospondin (Chen et al., 1995; Good et al., 1990; O'Reilly et al., 1994). It is postulated that the angiogenic phenotype is the result of a net balance between these positive and negative regulators of neovascularization (Good et al., 1990; O'Reilly et al., 1994; Parangi et al., 1996; Rastinejad et al., 1989). Several other endogenous inhibitors of angiogenesis have been identified, although not all are associated with the presence of a tumor. These include, platelet factor 4 (Gupta et al., 1995; Maione et al., 1990), interferon-alpha, interferon-inducible protein 10 (Angiolillo et al., 1995; Strieter et al., 1995), which is induced by interleukin-12 and/or interferon-gamma (Voest et al., 1995), gro-beta (Cao et al., 1995), and the 16 kDa N-terminal fragment of prolactin (Clapp et al., 1993). The only known angiogenesis inhibitor which specifically inhibits endothelial cell proliferation is angiostatin protein (O'Reilly et al. 1994).

Angiostatin protein is an approximately 38 kiloDalton (kDa) specific inhibitor of endothelial cell proliferation. Angiostatin protein is an internal fragment of plasminogen containing at least three of the five kringles of plasminogen. Angiostatin protein has been shown to reduce tumor weight and to inhibit metastasis in certain tumor models. (O'Reilly et al., 1994). As it is used hereinafter, the term "angiostatin protein" refers to angiostatin protein as described above; peptide fragments of angiostatin protein that have endothelial cell proliferation inhibiting activity; and analogs of angiostatin protein that have substantial sequence homology (as defined herein) to the amino acid sequence of angiostatin protein, which have endothelial cell proliferation inhibiting activity.

SUMMARY OF THE INVENTION

The present invention relates to a novel protein inhibitor, and method for its use. The protein is a potent and specific inhibitor of endothelial proliferation and angiogenesis. Systemic therapy with the inhibitor causes a nearly complete suppression of tumor-induced angiogenesis, and it exhibits strong indirect anti-tumor activity.

The inhibitory protein has a molecular weight of approximately 18,000 to approximately 20,000 Daltons (18 to 20 kDa) and is capable of inhibiting endothelial cell proliferation in cultured endothelial cells. The protein can be further characterized by its preferred N-terminal amino acid sequence, the first twenty (20) of which are as follows:

```
His Thr His Gln Asp Phe Gln Pro Val Leu
 1   2   3   4   5   6   7   8   9  10

His Leu Val Ala Leu Asn Thr Pro Leu Ser
11  12  13  14  15  16  17  18  19  20

(SEQ ID NO:1)
```

A preferred endothelial cell proliferation inhibitor of the invention is a protein having the above-described characteristics, and which can be isolated and purified from the murine hemangioendothelioma cell line EOMA. This inhibitory protein has been named endostatin protein.

The present invention provides methods and compositions for treating diseases and processes mediated by undesired and uncontrolled angiogenesis by administering to a human or animal with the undesired angiogenesis a composition comprising a substantially purified endostatin protein or endostatin protein derivative in a dosage sufficient to inhibit angiogenesis. The present invention is particularly useful for treating or for repressing the growth of tumors. Administration of endostatin protein to a human or animal with prevascularized metastasized tumors prevents the growth or expansion of those tumors.

The present invention also includes diagnostic methods and kits for detection and measurement of endostatin protein in biological fluids and tissues, and for localization of endostatin protein in tissues. The diagnostic method and kit can be in any configuration well known to those of ordinary skill in the art. The present invention also includes antibodies specific for the endostatin protein and antibodies that inhibit the binding of antibodies specific for the endostatin protein. These antibodies can be polyclonal antibodies or monoclonal antibodies. The antibodies specific for endostatin protein can be used in diagnostic kits to detect the presence and quantity of endostatin protein which is diagnostic or prognostic for the occurrence or recurrence of cancer or other disease mediated by angiogenesis. Antibodies specific for endostatin protein may also be administered to a human or animal to passively immunize the human or animal against endostatin protein, thereby reducing angiogenic inhibition.

The present invention also includes diagnostic methods and kits for detecting the presence and quantity of antibodies that bind endostatin protein in body fluids. The diagnostic method and kit can be in any configuration well known to those of ordinary skill in the art.

The present invention also includes endostatin peptide fragments that can be labeled isotopically or with other molecules or proteins for use in the detection and visualization of endostatin protein binding sites with state of the art techniques, including, but not limited to, positron emission tomography, autoradiography, flow cytometry, radioreceptor binding assays, and immunohistochemistry.

These endostatin peptides also act as agonists and antagonists at the endostatin protein receptor, thereby enhancing or blocking the biological activity of endostatin protein. Such peptides are used in the isolation of the endostatin protein receptor.

The present invention also includes endostatin protein, endostatin protein fragments, endostatin protein antisera, or endostatin receptor agonists and antagonists linked to cytotoxic agents for therapeutic and research applications.

The present invention includes molecular probes for the ribonucleic acid and deoxyribonucleic acid involved in transcription and translation of endostatin protein. These molecular probes provide means to detect and measure endostatin protein biosynthesis in tissues and cells.

A surprising discovery is that various forms of recombinant endostatin protein can serve as sustained release anti-angiogenesis compounds when administered to a tumor-bearing animal. A preferred form of the sustained release compound is un-refolded recombinantly produced endostatin protein.

Additionally, the present invention encompasses nucleic acid sequences comprising corresponding nucleotide codons that code for the above disclosed amino acid sequence and for endostatin protein and endothelial cell proliferation inhibiting peptide fragments thereof.

The present invention also relates to methods of using the endostatin protein and peptide fragments, corresponding nucleic acid sequences, and antibodies that bind specifically to the inhibitor and its peptides, to diagnose endothelial cell-related diseases and disorders.

The invention further encompasses a method for identifying receptors specific for endostatin protein, and the receptor molecules identified and isolated thereby.

The invention also relates to a method for identifying novel enzymes capable of releasing endostatin protein from collagen type XVIII, and other molecules containing an endostatin protein amino acid sequence, and peptides thereof. Such endostatin protein producing enzymes are also an aspect of the invention.

An important medical method is a new form of birth control, wherein an effective amount of endostatin protein is administered to a female such that uterine endometrial vascularization is inhibited and embryo implantation cannot occur, or be sustained.

A particularly important aspect of the present invention is the discovery of a novel and effective method for treating angiogenesis-related diseases, particularly angiogenesis-dependent cancer, in patients, and for curing angiogenesis-dependent cancer in patients. The method unexpectedly provides the medically important result of inhibition of tumor growth and reduction of tumor mass. The method relates to the co-administration of the endostatin protein of the present invention and another anti-angiogenesis compound, preferably angiostatin protein. Accordingly, the present invention also includes formulations containing endostatin protein, and optionally angiostatin protein, which are effective for treating or curing angiogenesis-dependent cancers.

Accordingly, it is an object of the present invention to provide a composition comprising an endostatin protein.

It is another object of the present invention to provide a method of treating diseases and processes that are mediated by angiogenesis.

It is yet another object of the present invention to provide a diagnostic or prognostic method and kit for detecting the presence and amount of endostatin protein in a body fluid or tissue.

It is yet another object of the present invention to provide a method and composition for treating diseases and processes that are mediated by angiogenesis including, but not limited to, hemangioma, solid tumors, leukemia, metastasis, telangiectasia psoriasis scleroderma, pyogenic granuloma, myocardial angiogenesis, plaque neovascularization, coronary collaterals, cerebral collaterals, arteriovenous malformations, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, and placentation.

It is another object of the present invention to provide a composition for treating or repressing the growth of a cancer.

It is an object of present invention to provide a method for detecting and quantifying the presence of an antibody specific for an endostatin protein in a body fluid.

Still another object of the present invention is to provide a composition consisting of antibodies to endostatin protein that are selective for specific regions of the endostatin protein molecule.

It is another object of the present invention to provide a method for the detection or prognosis of cancer.

It is another object of the present invention to provide a composition for use in visualizing and quantitating sites of endostatin protein binding in vivo and in vitro.

It is yet another object of the present invention to provide a composition for use in detection and quantification of endostatin protein biosynthesis.

It is yet another object of the present invention to provide a therapy for cancer that has minimal side effects.

Still another object of the present invention is to provide a composition comprising endostatin protein or an endostatin peptide linked to a cytotoxic agent for treating or repressing the growth of a cancer.

These and other objects, features and advantages of the present invention will become apparent after a review of the following detailed description of the disclosed embodiments and the appended claims.

Conditioned media collected from confluent EOMA cells or base media was applied to bovine capillary endothelial cells with 1 ng/ml bFGF in a 72 hour proliferation assay. Endothelial cell proliferation was inhibited by the EOMA conditioned media. Each bar represents the mean±SEM.

Figure 2:
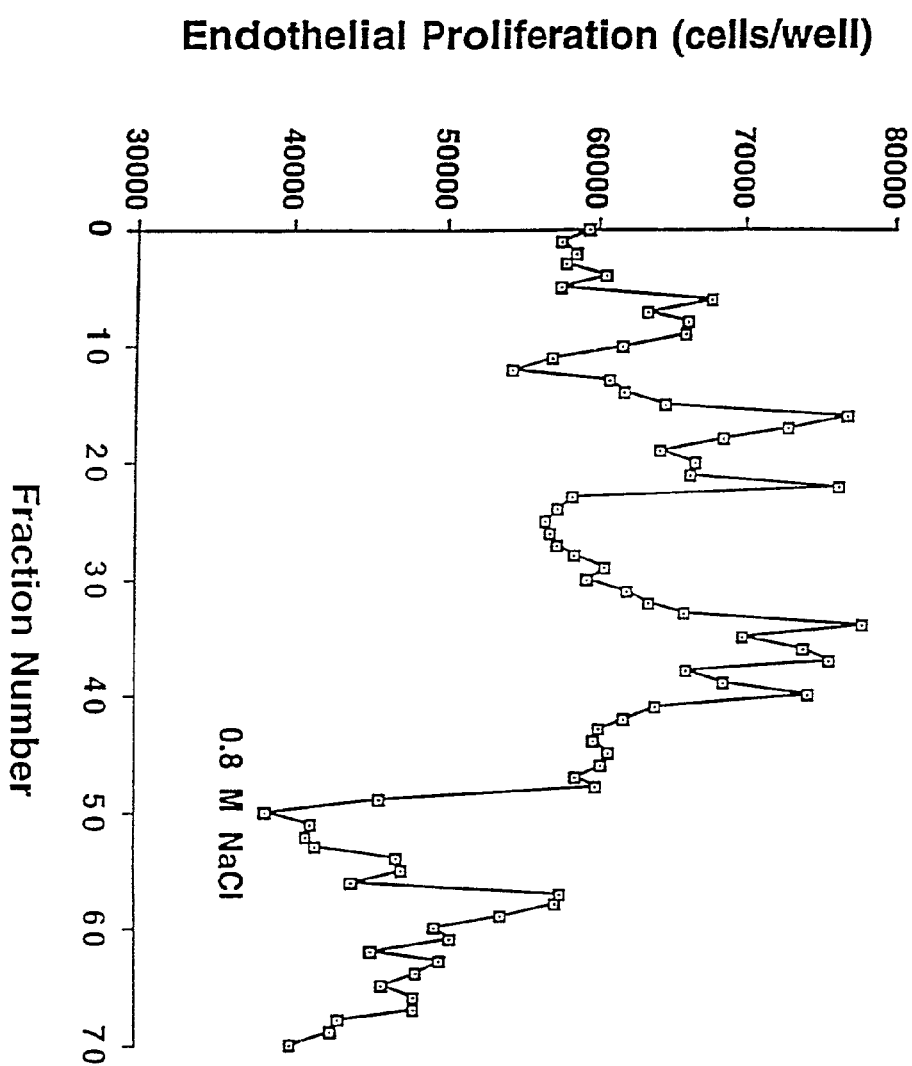

FIG. 2: Purification of an Inhibitor of Endothelial Proliferation from EOMA Conditioned Media.

Conditioned media collected from confluent EOMA cells was fractionated on a heparin sepharose column. Endothelial proliferation inhibiting activity eluted at approximately 0.8M NaCl.

Figure 3:
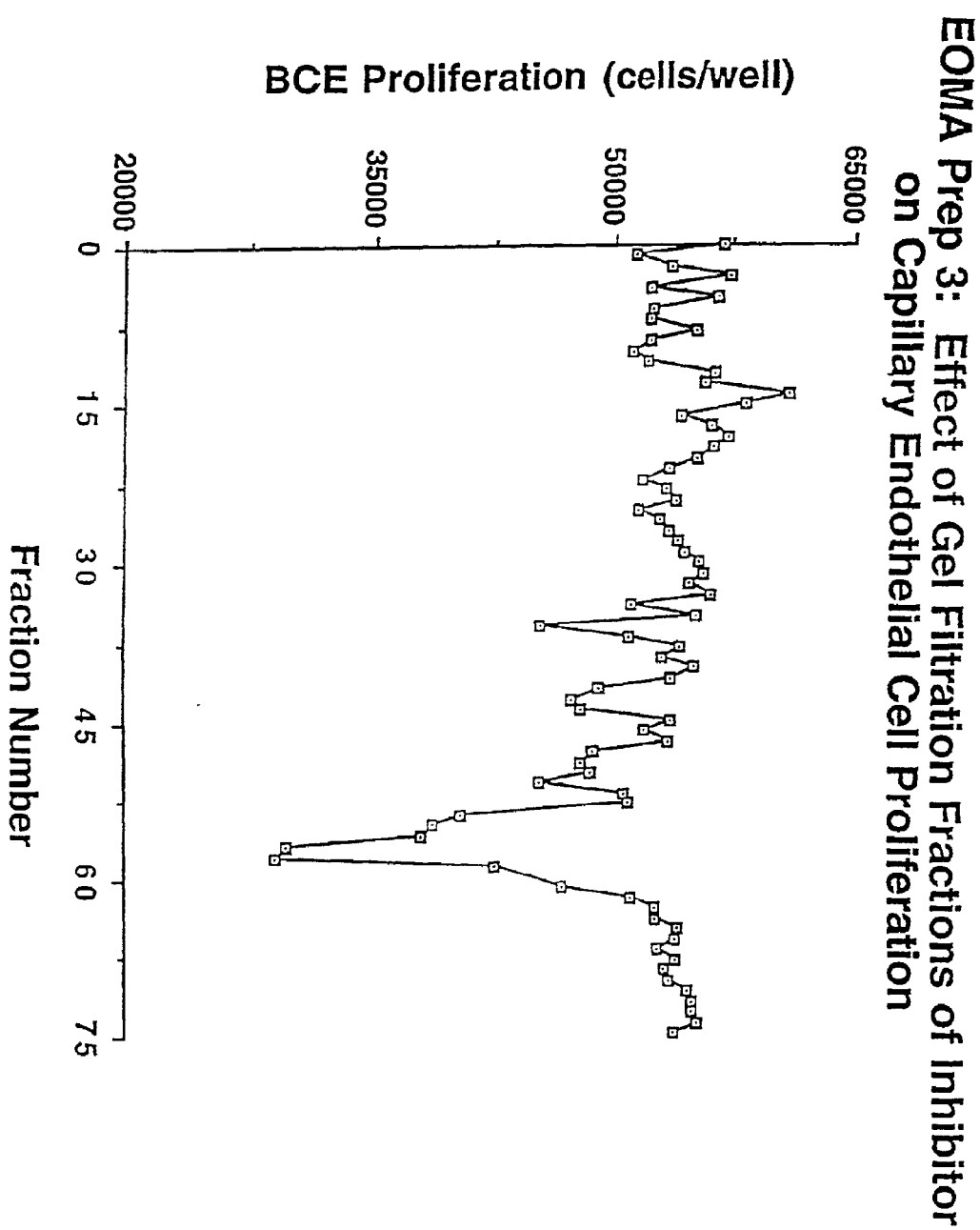

FIG. 3: Purification of an Inhibitor of Endothelial Proliferation by Gel Filtration.

Purified inhibitor from heparin sepharose column chromatography was applied to a gel filtration column and eluted as a single peak.

Figure 4:
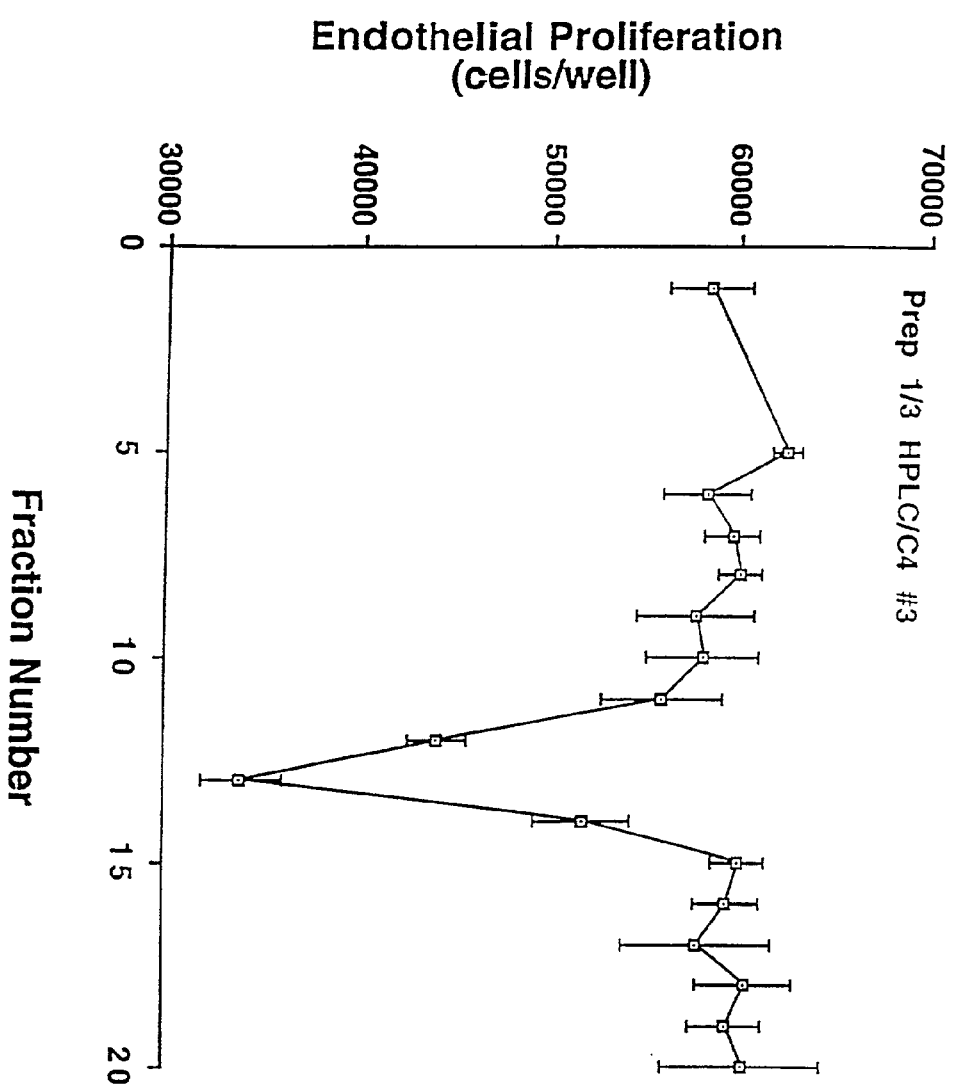

FIG. 4: Purification of Inhibitor of Endothelial Cell Proliferation by Reversed Phase Column Chromatography.

Inhibitor purified by heparin sepharose and gel filtration chromatography was applied to a reverse phase column. The inhibitor eluted as a single band from the column at approximately 45% of the acetonitrile.

Figure 5:
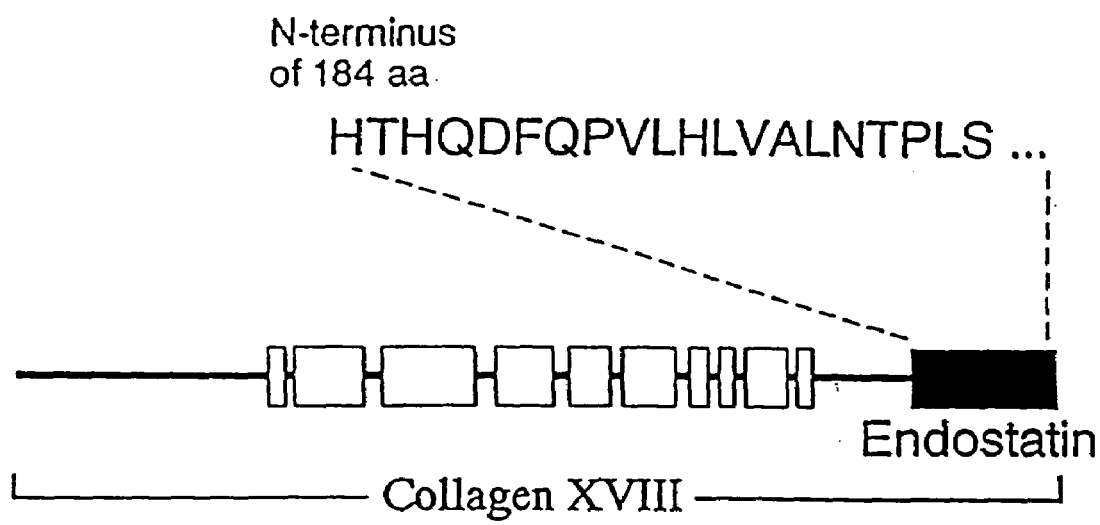

FIG. 5: N-terminal Amino Acid Sequence of An Inhibitor of Endothelial Cell Proliferation.

The N-terminal sequence of the purified inhibitor of endothelial cell proliferation is shown in relation to a schematic diagram of collagen type XVIII. The N-terminal sequence revealed identity of the inhibitor to an approximately 20 kDa C-terminal fragment (shown in solid shading) for collagen type XVIII. The open boxes represent the collagen-like domains of collagen type XVIII.

Figure 6:
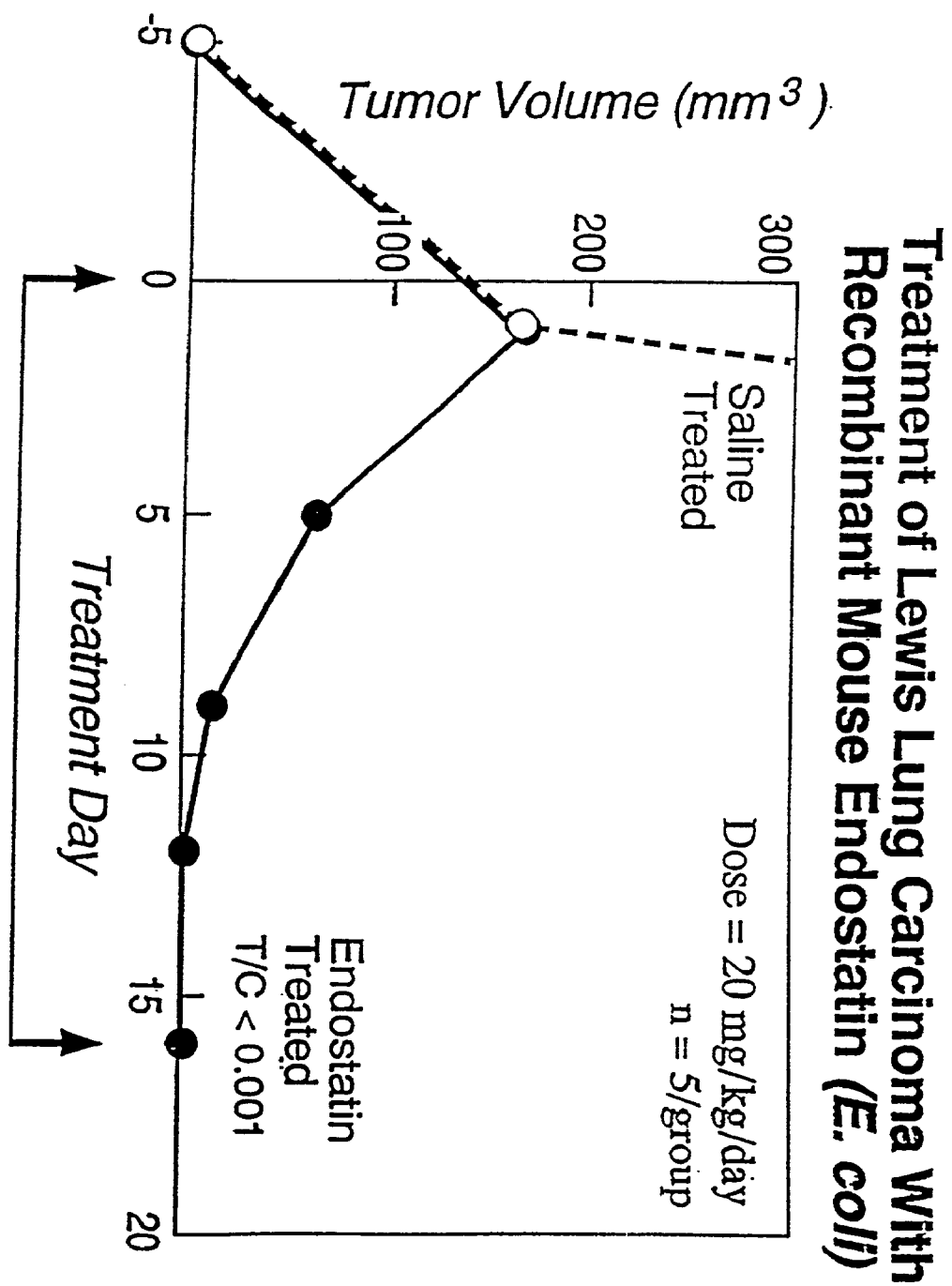

FIG. 6: Treatment of Lewis Lung Carcinoma With Recombinant Mouse endostatin protein Inhibitor.

Recombinant inhibitor produced in *E. coli* was administered to mice seeded with Lewis lung carcinoma that had achieved a tumor volume of approximately 150 mm$^3$. The inhibitor was administered at 20 mg/kg/day. Tumor mass regressed to non-detectable levels after approximately 12 days of treatment.

Figure 7:
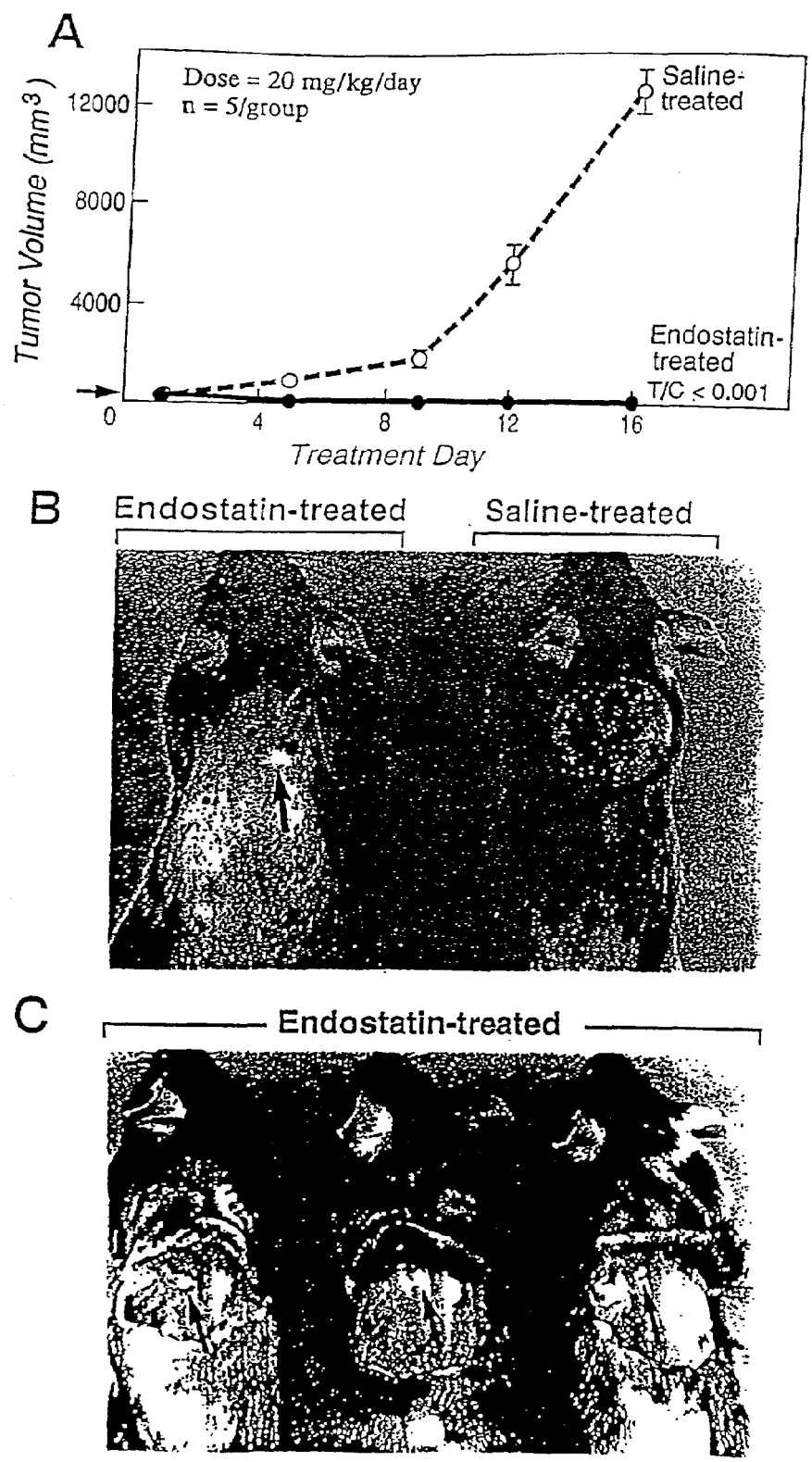

FIG. 7: Systemic Therapy with Recombinant endostatin protein Regresses Lewis Lung Carcinoma Primary Tumors.

(A) Mice were implanted subcutaneously on the dorsum with Lewis lung carcinoma cells. Systemic therapy with recombinant mouse endostatin protein (20 mg/kg/day) was begun when tumors were approximately 200 mm$^3$ (1% of body weight). Tumors in the mice treated with endostatin protein angiogenesis inhibitor rapidly regressed and were inhibited by >99% relative to saline-treated controls. Each point represents mean±SEM for 5 mice. The experiment was repeated with comparable results.

(B) Representative treated and untreated tumor-bearing mice after 11 days of systemic therapy with endostatin protein. Saline-treated mice (right) had rapidly growing red tumors with ulcerated surfaces. endostatin protein treated mice (left) had small pale residual tumors (arrow).

(C) Residual disease in endostatin protein treated mice. Three of the five endostatin protein treated mice were sacrificed after 16 days of therapy. Autopsy revealed small white residual tumors at the site of the original primary implantation (arrows).

Figure 8:
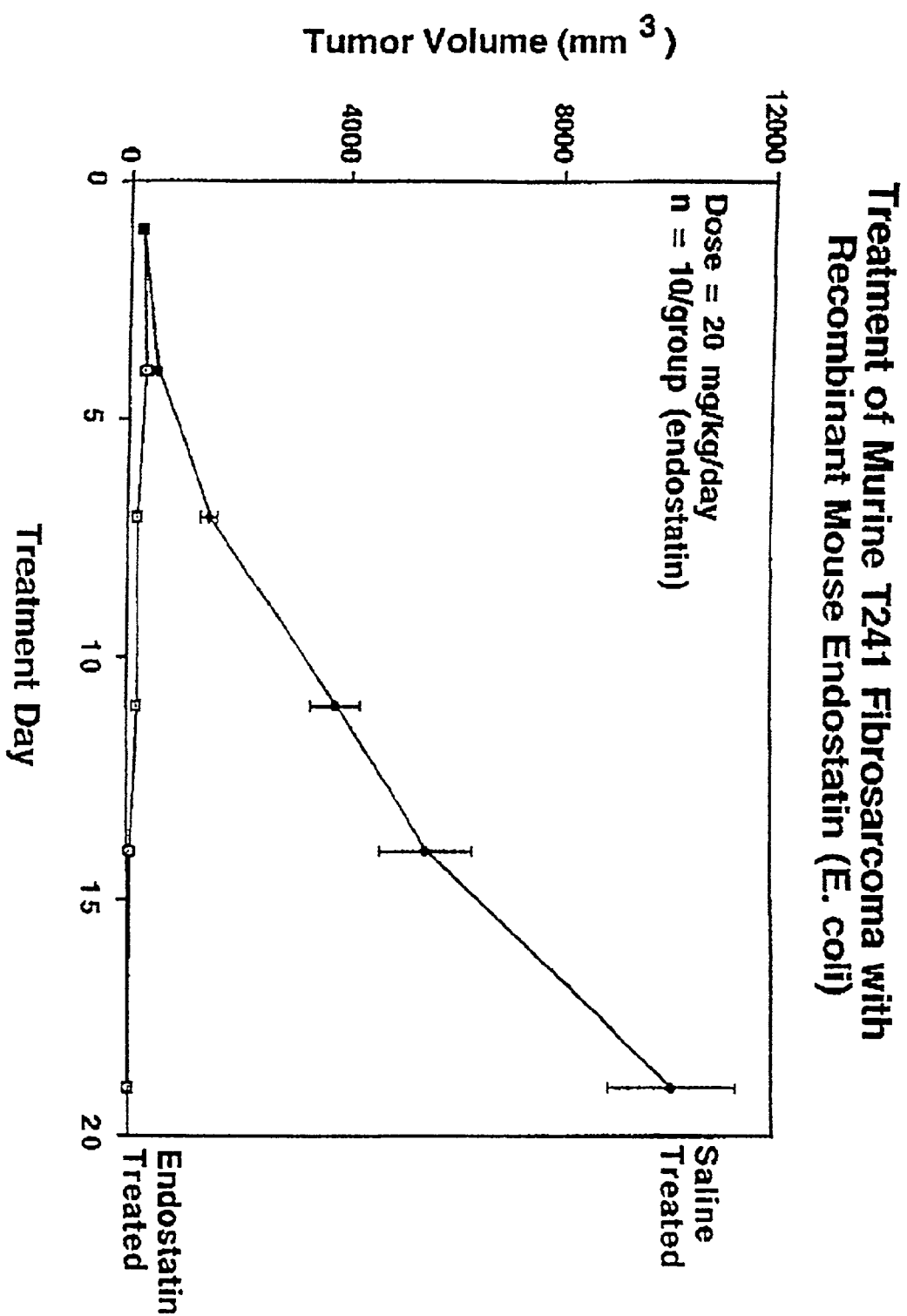

FIG. 8: Treatment of Murine T241 Fibrosarcoma with Recombinant Mouse endostatin protein from *E. coli*

Mice were seated with T241 Fibrosarcoma cells. Control mice were treated with saline. Experimental mice were treated with 20 mg/kg/day of recombinant mouse endostatin protein directed from *E. coli*.

Figure 9:
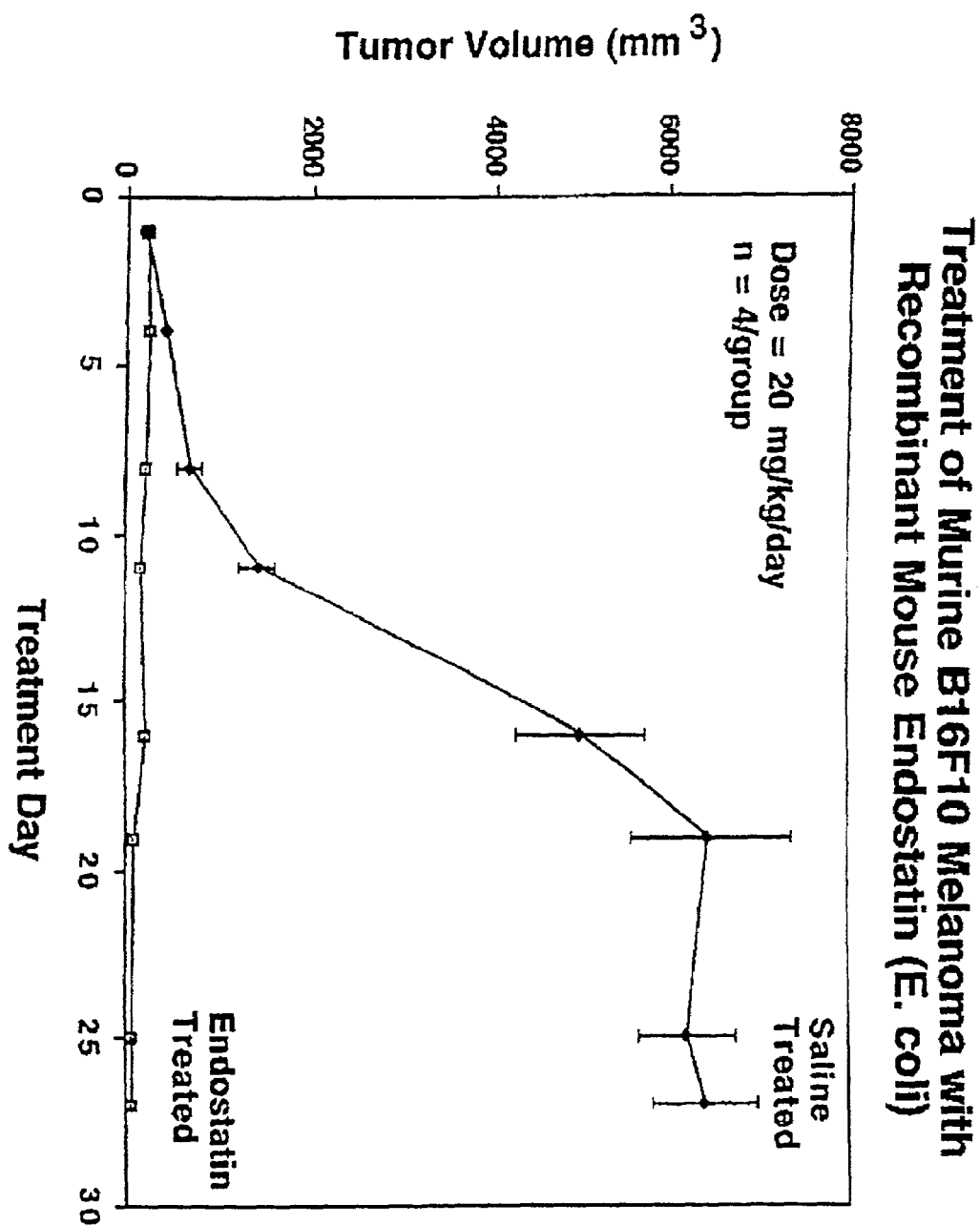

FIG. 9: Treatment of Murine B16F10 Melanoma with Recombinant Mouse endostatin protein from *E. coli*

Mice were seated with Murine B16F10 melanoma cells. Control animals were treated with saline. Experimental animals were treated with 20 mg/kg/day of recombinant mouse endostatin protein direct from *E. coli*.

Figure 10:
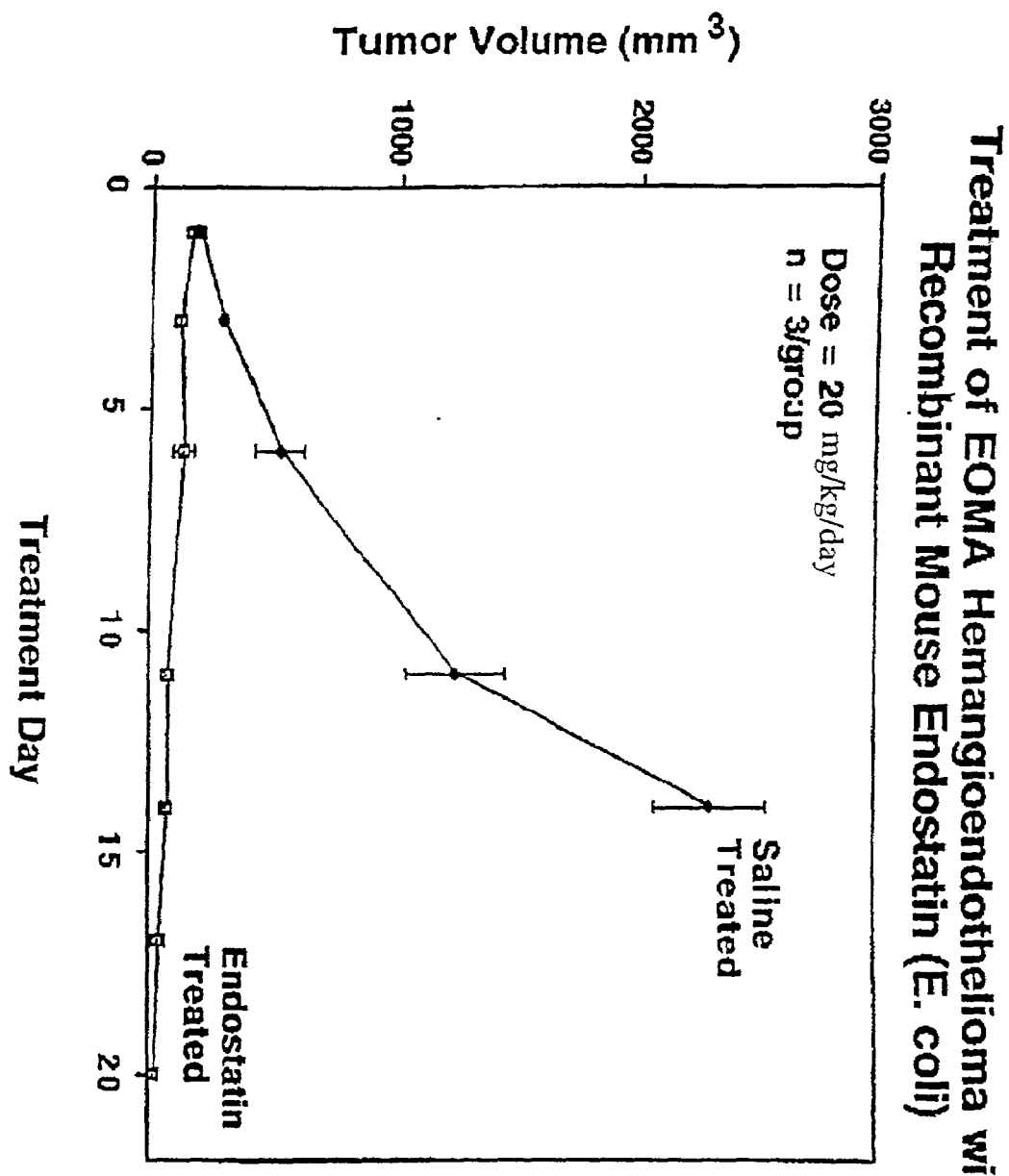

FIG. 10: Treatment of EOMA Hemangioendothelioma with Recombinant Mouse endostatin protein from *E. coli*

Mice were seated with EOMA hemangioendothelioma cells. Control animals were treated with saline. Experimental animals were treated with 20 mg/kg/day of Recombinant Mouse endostatin protein direct from *E. coli*.

Figure 11:
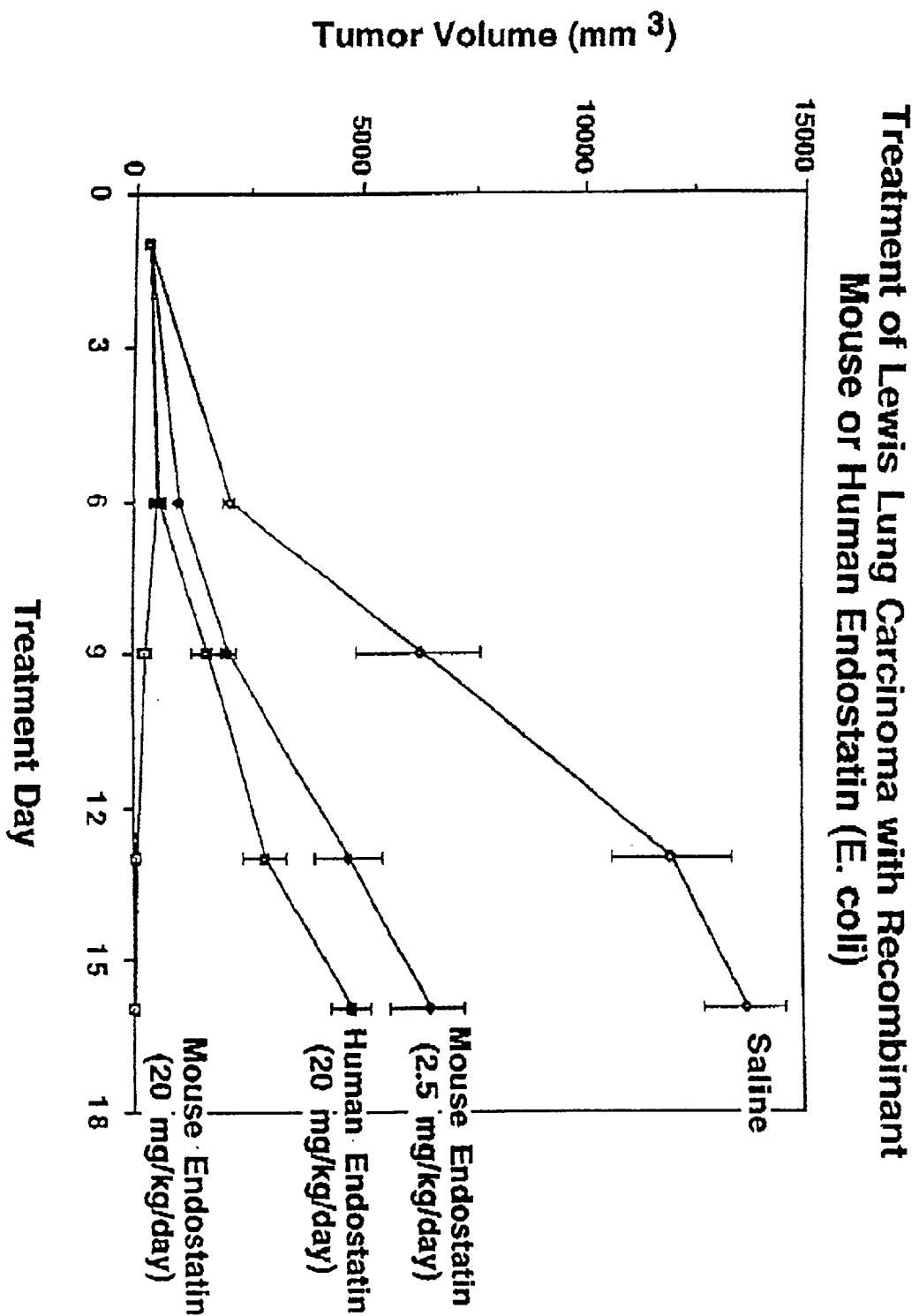

FIG. 11: Treatment of Lewis Lung Carcinoma with Recombinant Mouse or Human endostatin protein direct from *E. coli*.

Mice were seated with Lewis Lung Carcinoma cells. Control animals were treated with saline. Experimental animals were treated with Recombinant endostatin protein derived from the mouse sequence or Recombinant endostatin protein direct from the human sequence, wherein both endostatin protein are produced recombinantly in the *E. coli*. Mouse endostatin protein was administered at either 20 mg/kg/day or 2.5 mg/kg/day, and Human endostatin protein was administered at 20 mg/kg/day.

Figure 12:
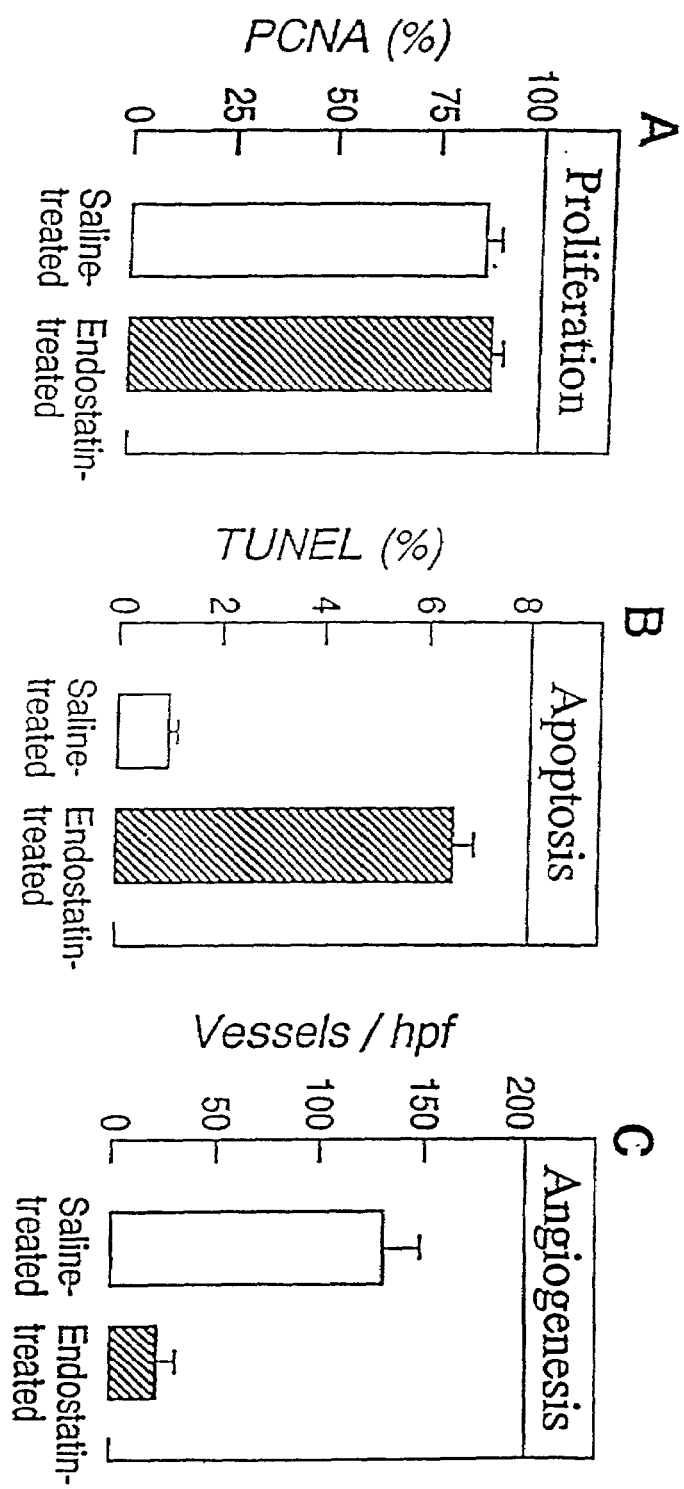

FIG. 12: Endostatin protein Results in an Inhibition of Angiogenesis and an Increase in Apoptosis of Lewis Lung Carcinoma Primary Tumors.

Histological sections of tumors from saline versus endostatin protein treated mice implanted with Lewis lung carcinomas were analyzed for proliferation (PCNA), apoptosis (TUNEL), and angiogenesis (vWF). There was no significant difference in the proliferative index of tumor cells (A) in treated versus untreated tumors. In contrast, the apoptotic index of the tumor cells (B) increased 8-fold ($p<0.001$) in the endostatin protein treated mice. Vessel density (C) was determined by counting the number of capillary blood vessels per high-power field (HPF) in sections stained with antibodies against vWF. Angiogenesis was almost completely suppressed in the residual microscopic tumors of the endostatin protein treated mice ($p<0.001$).

Figure 13:
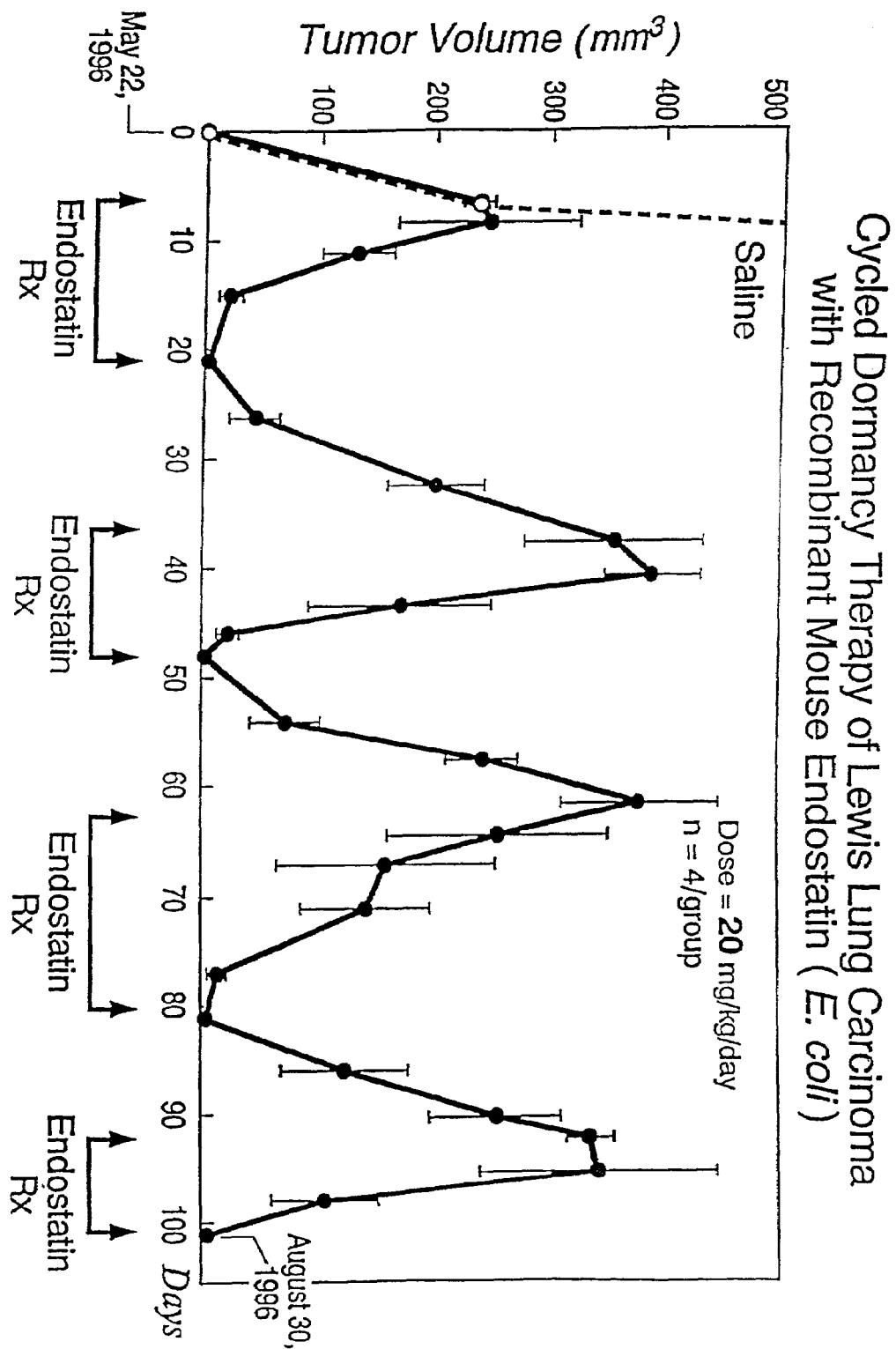

FIG. 13: Cycle Dormancy Therapy of Lewis Lung Carcinoma with Recombinant Mouse endostatin protein From *E. Coli*.

Mice were implanted subcutaneously on the dorsum with Lewis lung carcinoma cells. Systemic therapy with recombinant mouse inhibitor (endostatin protein), administered at a dose of 20 mg/kg/day, was begun when tumors were approximately 200 mm$^3$ (1% of body weight). Tumors in the mice treated with the endostatin protein inhibitor rapidly regressed to essentially non-detectable levels after approximately 15 days of therapy. When treatment was terminated the tumor volume increased rapidly and was subsequently treatable to the same non-detectable levels by reinitiation of treatment. The peaks and valleys in the figure show the cycling effect of inhibition with endostatin protein.

Figure 14:
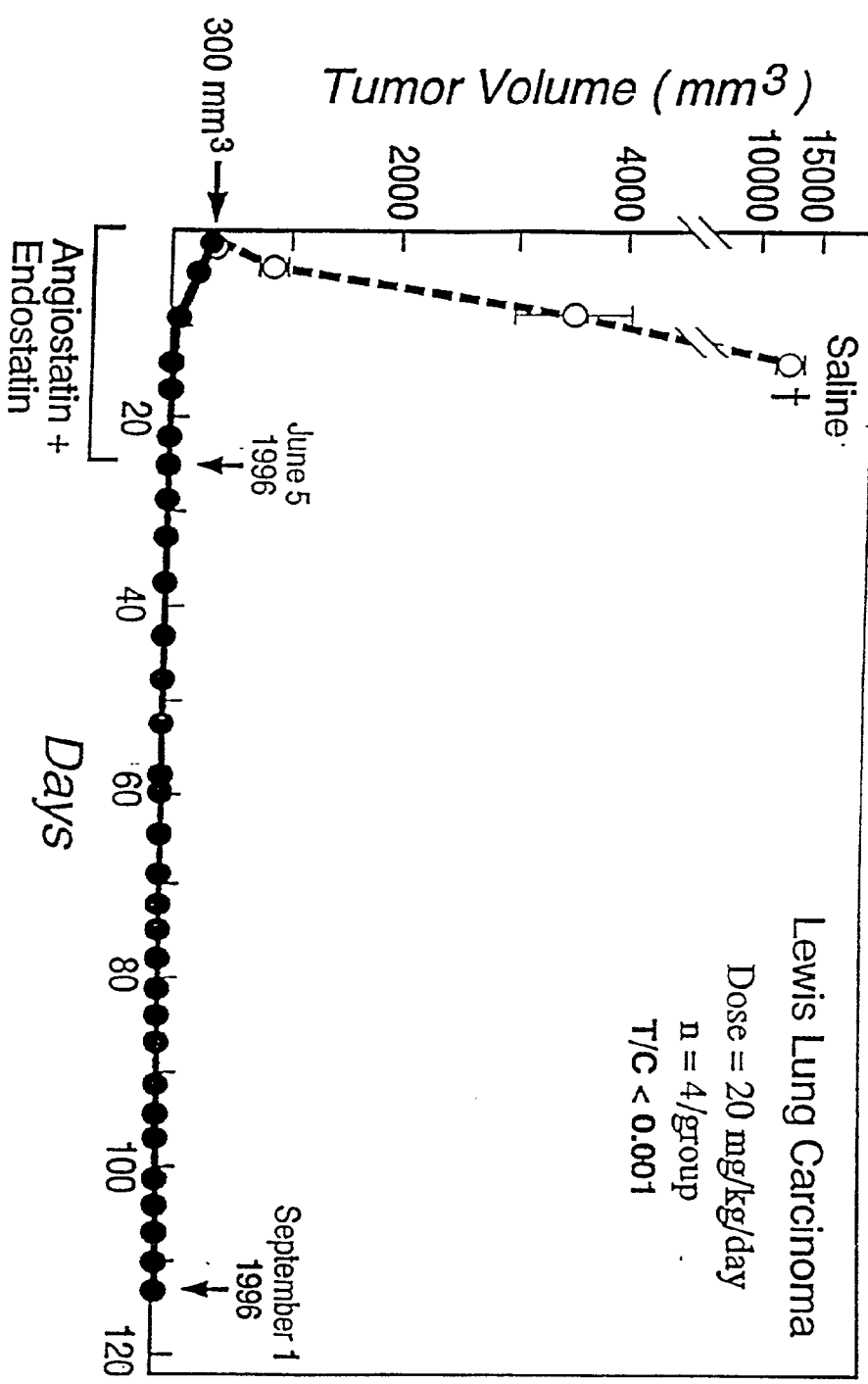

FIG. 14: Combination Therapy with Recombinant Mouse Angiostatin Protein and Endostatin Protein from *E. Coli*.

Mice were implanted subcutaneously on the dorsum with Lewis lung carcinoma cells. Systemic therapy with a combination of recombinant mouse endostatin protein (20 mg/kg/day) and recombinant mouse angiostatin protein (20 mg/kg/day) was begun when tumors were approximately 300 mm$^3$. Tumors in the mice treated with the combination therapy rapidly regressed to essentially non-detectable level in about 15 days. Importantly, the regressed tumors remained dormant and did not increase in size or mass after treatment was stopped. This is an unexpected result of substantial medical significance.

FIG. 15: Western Blotting Results of endostatin protein Antibodies.

(A) Western Blotting analysis revealed that mouse derived hybridomas produced monoclonal antibodies that recognize human endostatin protein recombinantly produced from *E. coli* (See arrow, lane 1).

(B) Western Blotting analysis revealed that rabbit derived polyclonal antibodies recognize human endostatin protein recombinantly produced from *E. coli* (See arrow, lane 1). These polyclonal antibodies showed cross-reactivity to mouse endostatin protein produced in *E. coli* (lane 2), and cross-reactivity to mouse collagen XV produced in *E. coli* (lane 3). FIGS. 15(A) and (B) represent the same membrane.

FIG. 16: Western Blotting Results from Rabbits A–F Producing Polyclonal endostatin protein Antibodies.

(A) Serum from rabbits A–C was used at a dilution of 1/500. The Figure shows that the polyclonal antibody reacts against recombinant mouse endostatin protein from *E. coli* non-induced (lane 1), induced (lane 2), and diluted 1:10 (lane 3).

(B) Serum from rabbits D–F was used at a dilution of 1/500. The Figure shows that the polyclonal antibody reacts against recombinant mouse endostatin protein from *E. coli* non-induced (lane 1), induced (lane 2), and diluted 1:10 (lane 3).

FIG. 17: Serum From Rabbits D and F (A) Ponceau S. Staining Results. Lanes (−) represent no protein loaded. Middle lanes (+) represent recombinant mouse endostatin protein produced by *E. coli*. Right lanes (+) represent recombinant human endostatin protein produced by *E. coli*.

(B) Western Blotting Results from Pre-Immune Serum Rabbits D and F. Lanes (−) represent no protein loaded. Middle lanes (+) represent recombinant mouse endostatin protein produced by *E. coli*. Right lanes (+) represent recombinant human endostatin protein produced by *E. coli*. No reactivity with mouse or human endostatin protein is detected.

Figure 18:
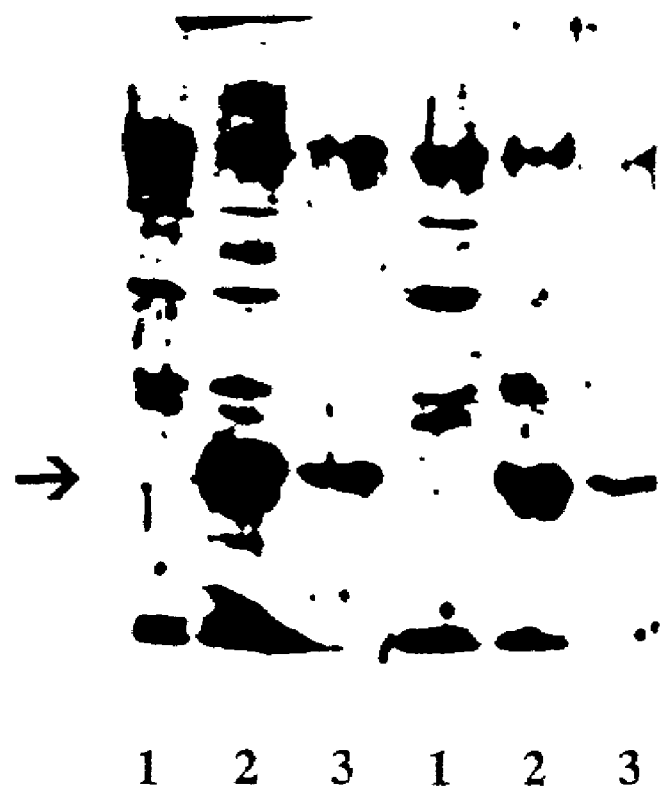

FIG. 18: Western Blotting Results from Immunized Rabbit F Demonstrating Cross-Reactivity to Recombinant Human endostatin protein (Left Three Lanes) and Recombinant Mouse Collagen XV (Right Three Lanes) Produced in *E. Coli*.

Rabbit F's serum was used to test for polyclonal antibody cross-reactivity against recombinant human endostatin protein produced by *E. coli* non-induced (left lane 1), induced (left lane 2), and diluted 1:10 (left lane 3); and against recombinant collagen XV from *E. coli* non-induced (right lane 1), induced (right lane 2), and diluted 1:10 (right lane 3).

DETAILED DESCRIPTION OF THE INVENTION

Applicants have discovered a new class of protein molecules that have the ability to inhibit endothelial proliferation when added to proliferating endothelial cells in vitro. Accordingly, these protein molecules have been functionally defined as endostatin proteins, however, it is to be understood that this functional definition is no way limits the bioactivity of endostatin proteins to inhibition of endothelial cell growth in vitro or in vivo. Many other functions of endostatin proteins are likely.

The term "endostatin protein" refers to a protein that is preferably 18 kDa to 20 kDa in size as determined by non-reduced and reduced gel electrophoresis, respectively. The term endostatin protein also includes precursor forms of the 18 kDa to 20 kDa protein. The term endostatin protein also includes fragments of the 18 kDa to 20 kDa protein and modified proteins and peptides that have a substantially similar amino acid sequence, and which are capable inhibiting proliferation of endothelial cells. For example, silent substitutions of amino acids, wherein the replacement of an amino acid with a structurally or chemically similar amino acid does not significantly alter the structure, conformation or activity of the protein, is well known in the art. Such silent substitutions are intended to fall within the scope of the appended claims.

It will be appreciated that the term "endostatin protein" includes shortened proteins or peptides wherein one or more amino acid is removed from either or both ends of endostatin protein, or from an internal region of the protein, yet the resulting molecule retains endothelial proliferation inhibiting activity. The term "endostatin protein" also includes lengthened proteins or peptides wherein one or more amino acid is added to either or both ends of endostatin protein, or to an internal location in the protein, yet the resulting molecule retains endothelial proliferation inhibiting activity. Such molecules, for example with tyrosine added in the first position are useful for labeling such as radioiodination with $^{125}$iodine for use in assays. Labeling with other radioisotopes may be useful in providing a molecular tool for destroying the target cell containing endostatin protein receptors. Other labeling with molecules such as ricin may provide a mechanism for destroying cells with endostatin protein receptors.

"Substantial sequence homology" means at least approximately 70% homology between amino acid residue sequence in the endostatin protein analog sequence and that of endostatin protein, preferably at least approximately 80% homology, more preferably at least approximately 90% homology.

Also included in the definition of the term endostatin protein are modifications of the endostatin protein, its subunits and peptide fragments. Such modifications include substitutions of naturally occurring amino acids at specific sites with other molecules, including but not limited to naturally and non-naturally occurring amino acids. Such substitutions may modify the bioactivity of endostatin protein and produce biological or pharmacological agonists or antagonists. The term endostatin protein also includes an N terminal fragment of endostatin protein consisting of the sequence of the first 20 N terminal amino acids which is shown in SEQ ID NO:1 and is shown in Table 1. This sequence of the first 20 N terminal amino acids corresponds to a C-terminal fragment of newly identified collagen type XVIII.

Table 1 shows the correspondence of 3 letter and 1 letter amino acid designations.

TABLE 1

| Amino Acid | Residue | Abbreviation |
| --- | --- | --- |
| 1 | HIS | H |
| 2 | THR | T |
| 3 | HIS | H |
| 4 | GLN | Q |
| 5 | ASP | D |
| 6 | PHE | F |
| 7 | GLN | Q |
| 8 | PRO | P |
| 9 | VAL | V |
| 10 | LEU | L |
| 11 | HIS | H |
| 12 | LEU | L |
| 13 | VAL | V |
| 14 | ALA | A |
| 15 | LEU | L |
| 16 | ASN | N |
| 17 | THR | T |

TABLE 1-continued

| Amino Acid | Residue | Abbreviation |
|---|---|---|
| 18 | PRO | P |
| 19 | LEU | L |
| 20 | SER | S |

The N-terminal amino acid sequence of endostatin protein corresponds to an internal 20 amino acid peptide fragment found in mouse collagen alpha 1 type XVIII starting at amino acid 1105 and ending at amino acid 1124. The N-terminal amino acid sequence of the inhibitor also corresponds to an internal 20 amino acid peptide fragment found in human collagen alpha 1 type XVIII starting at amino acid 1132 and ending at amino acid 1151.

Endostatin protein can be isolated from murine hemangioendothelioma EOMA. Endostatin protein may be produced from recombinant sources, from genetically altered cells implanted into animals, from tumors, and from cell cultures as well as other sources. It is anticipated that endostatin protein is made in cells of the nervous system. Endostatin protein can be isolated from body fluids including, but not limited to, serum, urine and ascites, or synthesized by chemical or biological methods (e.g. cell culture, recombinant gene expression, peptide synthesis, and in vitro enzymatic catalysis of precursor molecules to yield active endostatin protein). Recombinant techniques include gene amplification from DNA sources using the polymerase chain reaction (PCR), and gene amplification from RNA sources using reverse transcriptase/PCR.

Endostatin protein specifically and reversibly inhibits endothelial cell proliferation. The inhibitor protein molecules of the invention are useful as a birth control drug, and for treating angiogenesis-related diseases, particularly angiogenesis-dependent cancers and tumors. The protein molecules are also useful for curing angiogenesis-dependent cancers and tumors. The unexpected and surprising ability of these novel compounds to treat and cure angiogenesis-dependent cancers and tumors answers a long felt unfulfilled need in the medical arts, and provides an important benefit to mankind.

Important terms that are used herein are defined as follows. "Cancer" means angiogenesis-dependent cancers and tumors, i.e. tumors that require for their growth (expansion in volume and/or mass) an increase in the number and density of the blood vessels supplying then with blood. "Regression" refers to the reduction of tumor mass and size.

The endothelial proliferation inhibiting proteins of the present invention can be made by automated protein synthesis methodologies well known to one skilled in the art. Alternatively, endothelial proliferation inhibiting proteins, or endostatin proteins, of the present invention may be isolated from larger known proteins, such as human alpha 1 type XVIII collagen and mouse alpha 1 type XVIII collagen, proteins that share a common or similar N-terminal amino acid sequence. Examples of other potential endostatin protein source materials having similar N-terminal amino acid sequences include Bos taurus pregastric esterase, human alpha 1 type XV collagen, NAD-dependent formate dehydrogenase (EC 1.2.1.2) derived from Pseudomonas sp., s11459 hexon protein of bovine adenovirus type 3, CELF21D12 2 F21d12.3 Caenorhabditis elegans gene product, VAL1 TGMV AL1 protein derived from tomato golden mosaic virus, s01730 hexon protein derived from human adenovirus 12, Saccharomyces cerevisiae. For example, peptides closely related to endostatin protein may be derived from BOVMPE 1 pregastric esterase (BOS TAURUS) gene sequence corresponding to amino acids 502 to 521, and collagen alpha 1 type 15 from humans beginning at amino acid 316 ending at 335.

Proteins and peptides derived from these and other sources, including manual or automated protein synthesis, may be quickly and easily tested for endothelial proliferation inhibiting activity using a biological activity assay such as the bovine capillary erdothelial cell proliferation assay. Other bioassays for inhibiting activity include the chick CAM assay, the mouse corneal assay, and the effect of administering isolated or synthesized proteins on implanted tumors. The chick CAM assay is described by O'Reilly, et al. in "Angiogenic Regulation of Metastatic Growth" Cell, vol. 79 (2), Oct. 21, 1994, pp. 315–328, which is hereby incorporated by reference in its entirety. Briefly, 3 day old chicken embryos with intact yolks are separated from the egg and placed in a petri dish. After 3 days of incubation a methylcellulose disc containing the protein to be tested is applied to the CAM of individual embryos. After 48 hours of incubation, the embryos and CAMs are observed to determine whether endothelial growth has been inhibited. The mouse corneal assay involves implanting a growth factor-containing pellet, along with another pellet containing the suspected endothelial growth inhibitor, in the cornea of a mouse and observing the pattern of capillaries that are elaborated in the cornea.

Applicants' invention also encompasses nucleic acid sequences that correspond to and code for the endothelial proliferation-inhibiting protein molecules of the invention, and to monoclonal and polyclonal antibodies that bind specifically to such protein molecules. The biologically active protein molecules, nucleic acid sequences corresponding to the proteins, and antibodies that bind specifically to the proteins of the present invention are useful for modulating endothelial processes in vivo, and for diagnosing and treating endothelial cell-related diseases, for example by gene therapy.

Nucleic acid sequences that correspond to, and code for, endostatin protein and endostatin protein analogs can be prepared based upon the knowledge of the amino acid sequence, and the art recognized correspondence between codons (sequences of three nucleic acid bases), and amino acids. Because of the degeneracy of the genetic code, wherein the third base in a codon may vary yet still code for the same amino acid, many different possible coding nucleic acid sequences are derivable for any particular protein or peptide fragment.

Nucleic acid sequences are synthesized using automated systems well known in the art. Either the entire sequence may be synthesized or a series of smaller oligonucleotides are made and subsequently ligated together to yield the full length sequence. Alternatively, the nucleic acid sequence may be derived from a gene bank using oligonucleotides probes designed based on the N-terminal amino acid sequence and well known techniques for cloning genetic material.

The present invention also includes the detection of endostatin protein in body fluids and tissues for the purpose of diagnosis or prognosis of angiogenesis-mediated diseases such as cancer. The present invention also includes the detection of endostatin protein binding sites and receptors in cells and tissues. The present invention also includes methods of treating or preventing angiogenic diseases and processes including, but not limited to, arthritis and tumors by stimulating the production of endostatin protein, and/or by administering substantially purified endostatin protein, or endostatin protein agonists or antagonists, and/or endostatin protein antisera or antisera directed against endostatin protein antisera to a patient. Additional treatment methods include administration of endostatin protein, endostatin protein fragments, endostatin protein antisera, or endostatin protein receptor agonists and antagonists linked to cytotoxic agents. It is to be understood that the endostatin protein can be animal or human in origin. Endostatin protein can also be produced synthetically by chemical reaction or by recombinant techniques in conjunction with expression systems. endostatin protein can also be produced by enzymatically cleaving different molecules, including endostatin protein precursors, containing sequence homology or identity with segments of endostatin protein to generate peptides having anti-angiogenesis activity.

Passive antibody therapy using antibodies that specifically bind endostatin protein can be employed to modulate endothelial-dependent processes such as reproduction, development, and wound healing and tissue repair. In addition, antisera directed to the Fab regions of endostatin protein antibodies can be administered to block the ability of endogenous endostatin protein antisera to bind endostatin protein.

Antibodies specific for endostatin protein and endostatin protein analogs are made according to techniques and protocols well known in the art. The antibodies may be either polyclonal or monoclonal. The antibodies are utilized in well know immunoassay formats, such as competitive and non-competitive immunoassays, including ELISA, sandwich immunoassays and radioimmunoassays (RIAs), to determine the presence or absence of the endothelial proliferation inhibitors of the present invention in body fluids. Examples of body fluids include but are not limited to blood, serum, peritoneal fluid, pleural fluid, cerebrospinal fluid, uterine fluid, saliva, and mucus.

The proteins, nucleic acid sequences and antibodies of the present invention are useful for diagnosing and treating endothelial cell-related diseases and disorders. A particularly important endothelial cell process is angiogenesis, the formation of blood vessels. Angiogenesis-related diseases may be diagnosed and treated using the endothelial cell proliferation inhibiting proteins of the present invention. Angiogenesis-related diseases include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; teleangiectasia; hemophiliac joints; angiofibroma; and wound granulation. The endothelial cell proliferation inhibiting proteins of the present invention are useful in the treatment of disease of excessive or abnormal stimulation of endothelial cells. These diseases include, but are not limited to, intestinal adhesions, atherosclerosis, scleroderma, and hypertrophic scars, i.e., keloids. They are also useful in the treatment of diseases that have angiogenesis as a pathologic consequence such as cat scratch disease (*Rochele minalia quintosa*) and ulcers (*Helobacter pylori*).

The endothelial cell proliferation inhibiting proteins can be used as a birth control agent by reducing or preventing uterine vascularization required for embryo implantation.

Thus, the present invention provides an effective birth control method when an amount of the inhibitory protein sufficient to prevent embryo implantation is administered to a female. In one aspect of the birth control method, an amount of the inhibiting protein sufficient to block embryo implantation is administered before or after intercourse and fertilization have occurred, thus providing an effective method of birth control, possible a "morning after" method. While not wanting to be bound by this statement, it is believed that inhibition of vascularization of the uterine endometrium interferes with implantation of the blastocyst. Similar inhibition of vascularization of the mucosa of the uterine tube interferes with implantation of the blastocyst, preventing occurrence of a tubal pregnancy. Administration methods may include, but are not limited to, pills, injections (intravenous, subcutaneous, intramuscular), suppositories, vaginal sponges, vaginal tampons, and intrauterine devices. It is also believed that endostatin protein administration will interfere with normal enhanced vascularization of the placenta, and also with the development of vessels within a successfully implanted blastocyst and developing embryo and fetus.

Conversely, blockade of endostatin protein receptors with endostatin protein analogs which act as receptor antagonists may promote endothelialization and vascularization. Such effects may be desirable in situations of inadequate vascularization of the uterine endometrium and associated infertilty, wound repair, healing of cuts and incisions, treatment of vascular problems in diabetics, especially retinal and peripheral vessels, promotion of vascularization in transplanted tissue including muscle and skin, promotion of vascularization of cardiac muscle especially following transplantation of a heart or heart tissue and after bypass surgery, promotion of vascularization of solid and relatively avascular tumors for enhanced cytotoxin delivery, and enhancement of blood flow to the nervous system, including but not limited to the cerebral cortex and spinal cord.

A surprising discovery is that un-refolded and non-soluble recombinant endostatin protein is also a potent anti-angiogenesis compound which serves as a sustained release depot when administered to a patient.

The present invention also relates to methods of using endostatin protein and endothelial cell proliferation inhibiting peptide fragments of endostatin protein, nucleic acid sequences corresponding to endostatin protein and active peptide fragments thereof, and antibodies that bind specifically to endostatin protein and its peptides, to diagnose endothelial cell-related diseases and disorders.

The invention further encompasses a method for identifying endostatin protein-specific receptors, and the receptor molecules identified and isolated thereby.

The present invention also provides a method for quantitation of endostatin protein receptors.

A particularly important aspect of the present invention is the discovery of a novel and effective method for treating and curing angiogenesis-dependent cancer in patients. It was unexpectedly found that the co-administration of endostatin protein and angiostatin protein in an amount sufficient to inhibit tumor growth and cause sustainable regression of tumor mass to microscopic size cures angiogenesis-dependent cancer. Accordingly, the present invention also includes formulations effective for treating or curing angiogenesis-dependent cancers and tumors.

More particularly, recombinant mouse endostatin protein, from insect cells or *E. coli*, potently inhibits angiogenesis and the growth of metastases and primary tumors. In a novel method of sustained release, the *E. coli*-derived recombinant endostatin protein was administered as an un-refolded suspension in an amount sufficient to inhibit angiogenesis, thereby inhibiting tumor growth. Tumor mass was reduced when recombinant endostatin protein was administered in an amount sufficient to cause regression of the tumor. Primary tumors of 1–2% of body weight regressed by greater than 150-fold to become microscopic dormant lesions when treated by endostatin protein. Immunohistochemical analysis of the dormant tumors revealed blocked angiogenesis accompanied by high proliferation of the tumor cells balanced by a high rate of tumor cell apoptosis. There was no evidence of toxicity in any of the mice treated with endostatin protein.

It is contemplated as part of the present invention that endostatin protein can be isolated from a body fluid such as blood or urine of patients or the endostatin protein can be produced by recombinant DNA methods or synthetic peptide chemical methods that are well known to those of ordinary skill in the art. Protein purification methods are well known in the art and a specific example of a method for purifying endostatin protein, and assaying for inhibitor activity is provided in the examples below. Isolation of human endogenous endostatin protein is accomplished using similar techniques.

One example of a method of producing endostatin protein using recombinant DNA techniques entails the steps of (1) identifying and purifying an endostatin protein as discussed above, and as more fully described below, (2) determining the N-terminal amino acid sequence of the purified inhibitor, (3) synthetically generating a DNA oligonucleotide probe that corresponds to the N-terminal amino acid sequence, (4) generating a DNA gene bank from human or other mammalian DNA, (5) probing the gene bank with the DNA oligonucleotide probe, (6) selecting clones that hybridize to the oligonucleotide, (7) isolating the inhibitor gene from the clone, (8) inserting the gene into an appropriate vector such as an expression vector, (9) inserting the gene-containing vector into a microorganism or other expression system capable of expressing the inhibitor gene, and (10) isolating the recombinantly produced inhibitor. The above techniques are more fully described in laboratory manuals such as "Molecular Cloning: A Laboratory Manual" Second Edition by Sambrook et al., Cold Spring Harbor Press, 1989.

The gene for endostatin protein may also be isolated from cells or tissue (such as tumor cells) that express high levels of endostatin protein by (1) isolating messenger RNA from the tissue, (2) using reverse transcriptase to generate the corresponding DNA sequence and then (3) using PCR with the appropriate primers to amplify the DNA sequence coding for the active endostatin protein amino acid sequence.

Yet another method of producing endostatin protein, or biologically active fragments thereof, is by peptide synthesis. Once a biologically active fragment of an endostatin protein is found using the assay system described more fully below, it can be sequenced, for example by automated peptide sequencing methods. Alternatively, once the gene or DNA sequence which codes for endostatin protein is isolated, for example by the methods described above, the DNA sequence can be determined, which in turn provides information regarding the amino acid sequence. Thus, if the biologically active fragment is generated by specific methods, such as tryptic digests, or if the fragment is N-terminal sequenced, the remaining amino acid sequence can be determined from the corresponding DNA sequence.

Once the amino acid sequence of the peptide is known, for example the N-terminal 20 amino acids, the fragment can be synthesized by techniques well known in the art, as exemplified by "Solid Phase Peptide Synthesis: A Practical Approach" E. Atherton and R. C. Sheppard, IRL Press, Oxford England. Similarly, multiple fragments can be synthesized which are subsequently linked together to form larger fragments. These synthetic peptide fragments can also be made with amino acid substitutions at specific locations in order to test for agonistic and antagonistic activity in vitro and in vivo. Peptide fragments that possess high affinity binding to tissues can be used to isolate the endostatin protein receptor on affinity columns. Isolation and purification of the endostatin protein receptor is a fundamental step towards elucidating the mechanism of action of endostatin protein. This facilitates development of drugs to modulate the activity of the endostatin protein receptor, the final pathway to biological activity. Isolation of the receptor enables the construction of nucleotide probes to monitor the location and synthesis of the receptor, using in situ and solution hybridization technology.

Endostatin protein is effective in treating diseases or processes that are mediated by, or involve, angiogenesis. The present invention includes the method of treating an angiogenesis mediated disease with an effective amount of endostatin protein or endostatin protein agonists and antagonists. The angiogenesis mediated diseases include, but are not limited to, solid tumors; blood born tumors such as leukemias; tumor metastasis; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. endostatin protein is useful in the treatment of disease of excessive or abnormal stimulation of endothelial cells. These diseases include, but are not limited to, intestinal adhesions, atherosclerosis, scleroderma, and hypertrophic scars, i.e., keloids. endostatin protein can be used as a birth control agent by preventing vascularization required for blastocyst implantation and for development of the placenta, the blastocyst, the embryo and the fetus.

The synthetic peptide fragments of endostatin protein have a variety of uses. The peptide that binds to the endostatin protein receptor with high specificity and avidity is radiolabeled and employed for visualization and quantitation of binding sites using autoradiographic and membrane binding techniques. This application provides important diagnostic and research tools. Knowledge of the binding properties of the endostatin protein receptor facilitates investigation of the transduction mechanisms linked to the receptor.

In addition, labeling these peptides with short lived isotopes enables visualization of receptor binding sites in vivo using positron emission tomography or other modern radiographic techniques in order to locate tumors with endostatin protein binding sites.

Systematic substitution of amino acids within these synthesized peptides yields high affinity peptide agonists and antagonists to the endostatin protein receptor that enhance or diminish endostatin protein binding to its receptor. Such agonists are used to suppress the growth of micrometastases, thereby limiting the spread of cancer. Antagonists to endostatin protein are applied in situations of inadequate vascularization, to block the inhibitory effects of angiostatin protein and possibly promote angiogenesis. This treatment may have therapeutic effects to promote wound healing in diabetics.

Endostatin proteins are employed to develop affinity columns for isolation of the endostatin protein receptor from cultured tumor cells. Isolation and purification of the endostatin protein receptor is followed by amino acid sequencing. Next, nucleotide probes are developed for insertion into vectors for expression of the receptor. These techniques are well known to those skilled in the art. Transfection of the endostatin protein receptor into endothelial cells enhances the responsiveness of these cells to endogenous or exogenous endostatin protein and thereby decreasing the rate of metastatic growth.

Cytotoxic agents, such as ricin, are linked to endostatin protein, and high affinity endostatin peptide fragments, thereby providing a tool for destruction of cells that bind endostatin protein. These cells may be found in many locations, including but not limited to, micrometastases and primary tumors. Peptides linked to cytotoxic agents are infused in a manner designed to maximize delivery to the desired location. For example, ricin-linked high affinity endostatin protein fragments are delivered through a cannula into vessels supplying the target site or directly into the target. Such agents are also delivered in a controlled manner through osmotic pumps coupled to infusion cannulae.

According to the present invention, endostatin protein may be used in combination with other compositions and procedures for the treatment of diseases. For example, a tumor may be treated conventionally with surgery, radiation or chemotherapy combined with endostatin protein and then endostatin protein may be subsequently administered to the patient to extend the dormancy of micrometastases and to stabilize any residual primary tumor.

The endostatin protein of the present invention also can be used to generate antibodies that are specific for the inhibitor. The antibodies can be either polyclonal antibodies or monoclonal antibodies. These antibodies that specifically bind to the endostatin protein can be used in diagnostic methods and kits that are well known to those of ordinary skill in the art to detect or quantify the endostatin protein in a body fluid or tissue. Results from these tests can be used to diagnose or predict the occurrence or recurrence of a cancer and other angiogenesis mediated diseases.

The endostatin protein also can be used in a diagnostic method and kit to detect and quantify antibodies capable of binding endostatin protein. These kits would permit detection of circulating endostatin protein antibodies which indicates the spread of micrometastases in the presence of endostatin protein secreted by primary tumors in situ. Patients that have such circulating anti-endostatin protein antibodies may be more likely to develop tumors and cancers, and may be more likely to have recurrence of cancer after treatments or periods of remission. The Fab fragments of these anti-endostatin protein antibodies may be used as antigens to generate anti-endostatin protein Fab-fragment antisera which can be used to neutralize the removal of circulating endostatin protein by anti-endostatin protein antibodies.

Another aspect of the present invention is a method of blocking the action of excess endogenous endostatin protein. This can be done by passively immunizing a human or animal with antibodies specific for the undesired endostatin protein in the system. This treatment can be important in treating abnormal ovulation, menstruation and placentation, and vasculogenesis. This provides a useful tool to examine the effects of endostatin protein removal on metastatic processes. The Fab fragment of endostatin protein antibodies contains the binding site for endostatin protein. This fragment is isolated from endostatin protein antibodies using techniques known to those skilled in the art. The Fab fragments of endostatin protein antisera are used as antigens to generate production of anti-Fab fragment serum. Infusion of this antiserum against the Fab fragments of endostatin protein prevents endostatin protein from binding to endostatin protein antibodies. Therapeutic benefit is obtained by neutralizing endogenous anti-endostatin protein antibodies by blocking the binding of endostatin protein to the Fab fragments of anti-endostatin protein. The net effect of this treatment is to facilitate the ability of endogenous circulating endostatin protein to reach target cells, thereby decreasing the growth of metastases.

It is to be understood that the present invention is contemplated to include any derivatives of the endostatin protein that have endothelial inhibitory activity. The present invention includes the entire endostatin protein, derivatives of the endostatin protein and biologically-active fragments of the endostatin protein. These include proteins with endostatin protein activity that have amino acid substitutions or have sugars or other molecules attached to amino acid functional groups. The present invention also includes genes that code for endostatin protein and the endostatin protein receptor, and to proteins that are expressed by those genes.

The proteins and protein fragments with the endostatin protein activity described above can be provided as isolated and substantially purified proteins and protein fragments in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the endostatin protein may be incorporated into biodegradable polymers allowing for sustained release of the compound, the polymers being implanted in the vicinity of where drug delivery is desired, for example, at the site of a tumor or implanted so that the endostatin protein is slowly released systemically. Osmotic minipumps may also be used to provide controlled delivery of high concentrations of endostatin protein through cannulae to the site of interest, such as directly into a metastatic growth or into the vascular supply to that tumor. The biodegradable polymers and their use are described, for example, in detail in Brem et al., *J. Neurosurg.* 74:441–446 (1991), which is hereby incorporated by reference in its entirety.

The dosage of the endostatin protein of the present invention will depend on the disease state or condition being treated and other clinical factors such as weight and condition of the human or animal and the route of administration of the compound. For treating humans or animals, between approximately 0.5 mg/kilogram to 500 mg/kilogram of the endostatin protein can be administered. A more preferable range is 1 mg/kilogram to 100 mg/kilogram with the most preferable range being from 2 mg/kilogram to 50 mg/kilogram. Depending upon the half-life of the endostatin protein in the particular animal or human, the endostatin protein can be administered between several times per day to once a week. It is to be understood that the present invention has application for both human and veterinary use. The methods of the present invention contemplate single as well as multiple administrations, given either simultaneously or over an extended period of time.

The endostatin protein formulations include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The endostatin protein formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the present invention may include other agents conventional in the art having regard to the type of formulation in question.

Different peptide fragments of the intact endostatin protein molecule can be synthesized for use in several applications including, but not limited to the following; as antigens for the development of specific antisera, as agonists and antagonists active at endostatin protein binding sites, as peptides to be linked to cytotoxic agents for targeted killing of cells that bind endostatin protein. The amino acid sequences that comprise these peptides are selected on the basis of their position on the exterior regions of the molecule and are accessible for binding to antisera. The amino and carboxyl termini of endostatin protein, as well as the mid-region of the molecule are represented separately among the fragments to be synthesized. The amino terminus distal to the 20th amino acid and carboxyl termini of endostatin protein may contain or be modified to contain tyrosine and lysine residues and are labeled with many techniques. A tyrosine or lysine is added to fragments that do not have these residues to facilitate labeling of reactive amino and hydroxyl groups on the peptide. These peptide sequences are compared to known sequences using sequence data banks to determine potential sequence homologies. This information facilitates elimination of sequences that exhibit a high degree of sequence homology to other molecules, thereby enhancing the potential for high specificity in the development of antisera, agonists and antagonists to endostatin protein.

Peptides can be synthesized in a standard microchemical facility and purity checked with HPLC and mass spectrophotometry. Methods of peptide synthesis, HPLC purification and mass spectrophotometry are commonly known to those skilled in these arts.

Peptides and endostatin protein are also produced in recombinant E. coli, as described below, or in insect or yeast expression systems, and purified with column chromatography.

Endostatin protein and endostatin derived peptides can be coupled to other molecules using standard methods. The amino terminus distal to the 20th amino acid and the carboxyl terminus of endostatin protein may both contain tyrosine and lysine residues and are isotopically and nonisotopically labeled with many techniques, for example radiolabeling using conventional techniques (tyrosine residues-chloramine T, iodogen, lactoperoxidase; lysine residues-Bolton-Hunter reagent). These coupling techniques are well known to those skilled in the art. The coupling technique is chosen on the basis of the functional groups available on the amino acids including, but not limited to amino, sulfhydral, carboxyl, amide, phenol, and imidazole. Various reagents used to effect these couplings include among others, glutaraldehyde, diazotized benzidine, carbodiimide, and p-benzoquinone.

Endostatin peptides are chemically coupled to isotopes, enzymes, carrier proteins, cytotoxic agents, fluorescent molecules and other compounds for a variety of applications. The efficiency of the coupling reaction is determined using different techniques appropriate for the specific reaction. For example, radiolabeling of an endostatin peptide or protein with $^{125}$I is accomplished using chloramine T and $Na^{125}$, of high specific activity. The reaction is terminated with sodium metabisulfite and the mixture is desalted on disposable columns. The labeled peptide is eluted from the column and fractions are collected. Aliquots are removed from each fraction and radioactivity measured in a gamma counter. In this manner, the unreacted $Na^{125}I$ is separated from the labeled endostatin peptide. The peptide fractions with the highest specific radioactivity are stored for subsequent use such as analysis of the ability to bind to endostatin protein antisera.

Another application of peptide conjugation is for production of polyclonal antisera. For example, endostatin protein peptides containing lysine residues are linked to purified bovine serum albumin using glutaraldehyde. The efficiency of the reaction is determined by measuring the incorporation of radiolabeled peptide. Unreacted glutaraldehyde and peptide are separated by dialysis. The conjugate is stored for subsequent use.

Antiserum against endostatin protein can be generated. After peptide synthesis and purification, both monoclonal and polyclonal antisera are raised using established techniques known to those skilled in the art. For example, polyclonal antisera may be raised in rabbits, sheep, goats or other animals. endostatin protein peptides conjugated to a carrier molecule such as bovine serum albumin, or endostatin protein itself, is combined with an adjuvant mixture, emulsified and injected subcutaneously at multiple sites on the back, neck, flanks, and sometimes in the footpads. Booster injections are made at regular intervals, such as every 2 to 4 weeks. Blood samples are obtained by venipuncture, for example using the marginal ear veins after dilation, approximately 7 to 10 days after each injection. The blood samples are allowed to clot overnight at 4° C. and are centrifuged at approximately 2400 X g at 4° C. for about 30 minutes. The serum is removed, aliquoted, and stored at 4° C. for immediate use or at −20 to −90° C. for subsequent analysis.

All serum samples from generation of polyclonal antisera or media samples from production of monoclonal antisera are analyzed for determination of titer. Titer is established through several means, for example, using dot blots and density analysis, and also with precipitation of radiolabeled peptide-antibody complexes using protein A, secondary antisera, cold ethanol or charcoal-dextran followed by activity measurement with a gamma counter. The highest titer antisera are also purified on affinity columns which are commercially available. endostatin peptides are coupled to the gel in the affinity column. Antiserum samples are passed through the column and anti-endostatin protein antibodies remain bound to the column. These antibodies are subsequently eluted, collected and evaluated for determination of titer and specificity.

The highest titer endostatin protein antisera is tested to establish the following: a) optimal antiserum dilution for highest specific binding of the antigen and lowest non-specific binding, b) the ability to bind increasing amounts of endostatin peptide in a standard displacement curve, c) potential cross-reactivity with related peptides and proteins, including endostatin protein related species, d) ability to detect endostatin peptides in extracts of plasma, urine, tissues, and in cell culture media.

Kits for measurement of endostatin protein are also contemplated as part of the present invention. Antisera that possess the highest titer and specificity and can detect endostatin protein or peptides in extracts of plasma, urine, tissues, and in cell culture media are further examined to establish easy to use kits for rapid, reliable, sensitive, and specific measurement and localization of angiostatin protein. These assay kits include but are not limited to the following techniques; competitive and non-competitive assays, radioimmunoassays, bioluminescence and chemiluminescence assays, fluorometric assays, sandwich assays, immunoradiometric assays, dot blots, enzyme linked assays including ELISA, microtiter plates, antibody coated strips or dipsticks for rapid monitoring of urine or blood, and immunocytochemistry. For each kit the range, sensitivity, precision, reliability, specificity and reproducibility of the assay are established. Intraassay and interassay variation is established at 20%, 50% and 80% points on the standard curves of displacement or activity.

One example of an assay kit commonly used in research and in the clinic is a radioimmunoassay (RIA) kit. An endostatin protein RIA is illustrated below. After successful radioiodination and purification of endostatin protein or an endostatin peptide, the antiserum possessing the highest titer is added at several dilutions to tubes containing a relatively constant amount of radioactivity, such as 10,000 cpm, in a suitable buffer system. Other tubes contain buffer or preimmune serum to determine the non-specific binding. After incubation at 4 C for 24 hours, protein A is added and the tubes are vortexed, incubated at room temperature for 90 minutes, and centrifuged at approximately 2000–2500 X g at 4 C to precipitate the complexes of antibody bound to labeled antigen. The supernatant is removed by aspiration and the radioactivity in the pellets counted in a gamma counter. The antiserum dilution that binds approximately 10 to 40% of the labeled peptide after subtraction of the non-specific binding is further characterized.

Next, a dilution range (approximately 0.1 pg to 10 ng) of the endostatin peptide used for development of the antiserum is evaluated by adding known amounts of the peptide to tubes containing radiolabeled peptide and antiserum. After an additional incubation period, for example, 24 to 48 hours, protein A is added and the tubes centrifuged, supernatant removed and the radioactivity in the pellet counted. The displacement of the binding of radiolabeled endostatin peptide by the unlabeled endostatin peptide (standard) provides a standard curve. Several concentrations of other endostatin peptide fragments, plasminogen, endostatin protein from different species, and homologous peptides are added to the assay tubes to characterize the specificity of the endostatin protein antiserum.

Extracts of various tissues, including but not limited to, primary and secondary tumors, carcinomas, cultures of endostatin protein producing cells, placenta, uterus, and other tissues such as brain, liver, and intestine, are prepared using extraction techniques that have been successfully employed to extract endostatin protein. After lyophilization or Speed Vac of the tissue extracts, assay buffer is added and different aliquots are placed into the RIA tubes. Extracts of known endostatin protein producing cells produce displacement curves that are parallel to the standard curve, whereas extracts of tissues that do not produce endostatin protein do not displace radiolabeled endostatin protein from the endostatin protein antiserum. In addition, extracts of urine, plasma, and cerebrospinal fluid from animals with carcinomas are added to the assay tubes in increasing amounts. Parallel displacement curves indicate the utility of the endostatin protein assay to measure endostatin protein in tissues and body fluids.

Tissue extracts that contain endostatin protein are additionally characterized by subjecting aliquots to reverse phase HPLC. Eluate fractions are collected, dried in Speed Vac, reconstituted in RIA buffer and analyzed in the endostatin protein RIA. The maximal amount of endostatin protein immunoreactivity is located in the fractions corresponding to the elution position of endostatin protein.

The assay kit provides instructions, antiserum, endostatin protein or endostatin protein peptide, and possibly radiolabeled endostatin protein and/or reagents for precipitation of bound endostatin protein—endostatin protein antibody complexes. The kit is useful for the measurement of endostatin protein in biological fluids and tissue extracts of animals and humans with and without tumors.

Another kit is used for localization of endostatin protein in tissues and cells. This endostatin protein immunohistochemistry kit provides instructions, endostatin protein antiserum, and possibly blocking serum and secondary antiserum linked to a fluorescent molecule such as fluorescein isothiocyanate, or to some other reagent used to visualize the primary antiserum. Immunohistochemistry techniques are well known to those skilled in the art. This endostatin protein immunohistochemistry kit permits localization of endostatin protein in tissue sections and cultured cells using both light and electron microscopy. It is used for both research and clinical purposes. For example, tumors are biopsied or collected and tissue sections cut with a microtome to examine sites of endostatin protein production. Such information is useful for diagnostic and possibly therapeutic purposes in the detection and treatment of cancer.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Identification of an Inhibitor of Capillary Endothelial Cell Proliferation from Hemangioendothelioma Cells A murine hemangioendothelioma cell line, EOMA (Obeso et al., 1990), was evaluated for evidence of the production of inhibitors of endothelial cell proliferation. Many of the known endogenous inhibitors of angiogenesis inhibit the in vitro proliferation of endothelial cells.

Figure 1:
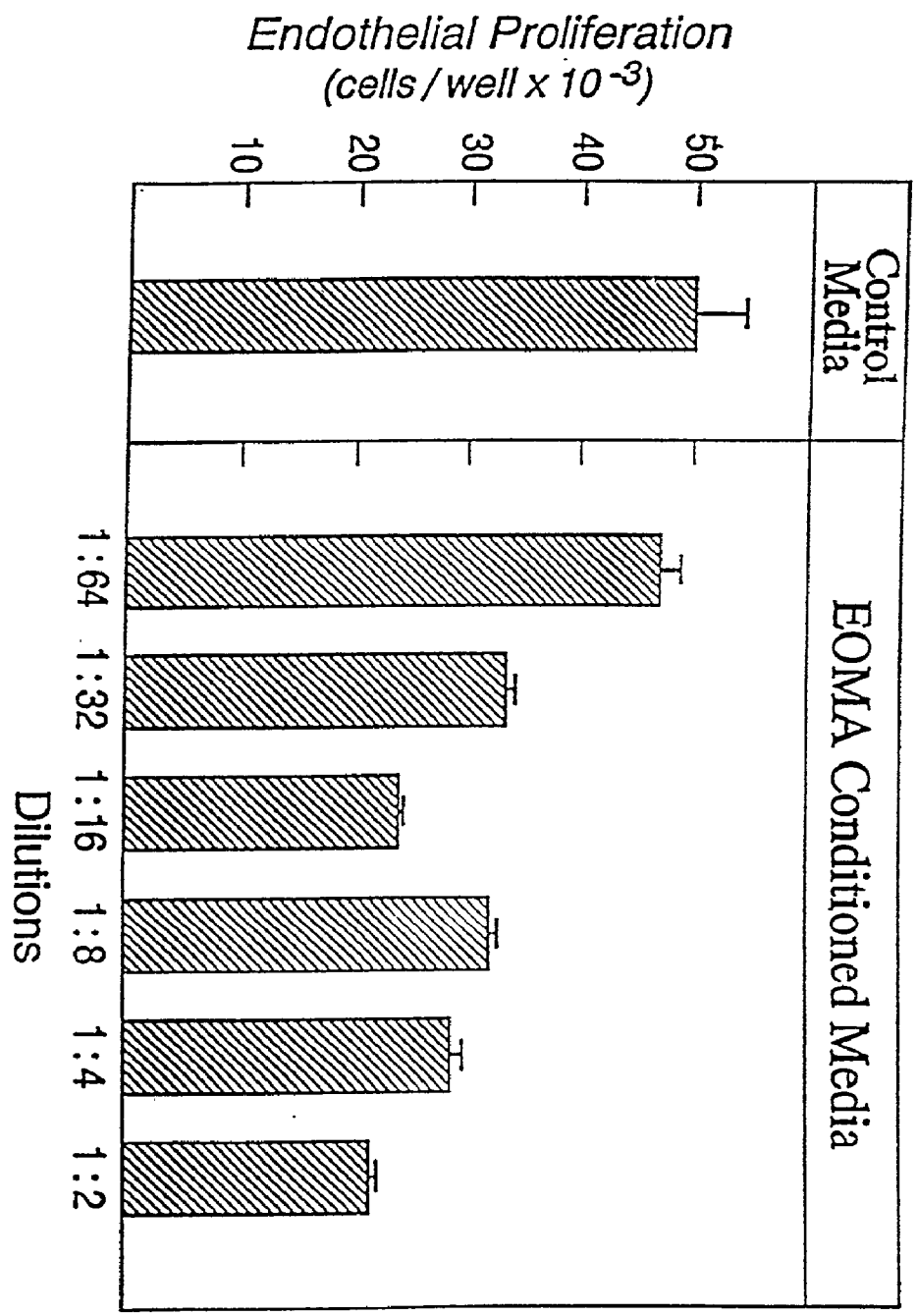
FIG. 1: Inhibition of Capillary Endothelial Cell Proliferation by Conditioned Media from EOMA Cells.

Conditioned Media Collection: Cells of the murine hemangioendothelioma cell line EOMA were maintained in DMEM supplemented with 10% bovine calf serum (BCS) and 1% glutamine-penicillin-streptomycin (GPS) in a 37° C. and 10% $CO_2$ incubator. Conditioned media from EOMA cells (i.e. culture media used to grow EOMA cells) was applied to bovine capillary endothelial cells, stimulated with bFGF, in a 72 hour proliferation assay. The conditioned media reversibly inhibited the proliferation of capillary endothelial cells as compared to controls. The pattern of inhibition was consistent with the presence of inhibitory and stimulatory activity of endothelial cell proliferation (FIG. 1).

EXAMPLE 2

Inhibitory Activity of Endothelial Cell Proliferation is not Due to Angiostatin Protein To determine if the inhibitor of capillary endothelial cell proliferation produced by the EOMA cells was angiostatin protein, pooled conditioned media was applied to a lysine column (lysine conjugated to Sepharose™ chromatography beads). Lysine Sepharose binds angiostatin protein and has been used for its purification (O'Reilly et al., 1996). The endothelial cell inhibitory activity was found only in the flowthrough fraction and not in the bound fraction (data not shown). The lack of binding of the inhibitory activity to lysine Sepharose suggested that the novel inhibitor of endothelial cell proliferation was not angiostatin protein.

EXAMPLE 3

Purification of a 20 kDa Protein from the Conditioned Media of EOMA Cells which Specifically inhibits Endothelial Cell Proliferation Because several angiogenesis inhibitors have an affinity for heparin, the flow-through from the lysine Sepharose column was applied to a heparin Sepharose column. The inhibitory activity bound heparin with relatively high affinity and was eluted with 0.6–0.8 M NaCl in 10 mM Tris pH 7.4, as shown in FIG. 2. To further purify the inhibitory activity, the sample was concentrated and applied to a gel filtration (Bio-Rad Bio-Gel P-100 fine gel or Pharmacia Sephacryl S-200HR gel) column (see FIG. 3), followed by several cycles of reverse-phase HPLC with a C4 column. The inhibitory activity was eluted from the C4 column with 40–45% acetonitrile in 0.1% trifluoroacetic acid, as exemplified by FIG. 4. After the final C4 column, the inhibitory activity was associated with a protein of molecular mass of approximately 20 kDa (reduced) or 18 kDa (non-reduced), by SDS-PAGE, purified to apparent homogeneity.

With respect to Examples 2 and 3, lysine Sepharose, heparin Sepharose, Sephacryl S-200 HR gel (Pharmacia, Uppsala, Sweden), Bio-Gel P-100 fine polyacrylamide gel (Bio-Rad Laboratories, Richmond, Calif.), and a SynChropak RP-4 (100×4.6 mm) C4 reverse-phase column (Synchrom, Inc., Lafayette, Ind.) were prepared according to the manufacturers recommendations. A heparin-Sepharose column (50×2.5 cm) was equilibrated with 50 mM NaCl 10 mM Tris-HCl pH 7.4. Pooled conditioned media was applied and the column was washed with the equilibration buffer. The column was eluted with a continuous gradient of 50 mM–2 M NaCl in 10 mM Tris-HCl at pH 7.4 (200 ml total volume) followed by 100 ml of 2 M NaCl in 10 mM Tris-HCl at pH 7.4. Fractions were collected and an aliquot of each was applied to capillary endothelial cells. Fractions which inhibited their proliferation were dialyzed (MWCO=6,000–8,000) against PBS and concentrated using a 4000 MWCO Nanospin concentrator (Gelman Sciences, Ann Arbor, Mich.).

A Bio-Gel P-100 column or a Sephacryl S-200 HR column (75×1.5 cm) was equilibrated with PBS. The sample from heparin Sepharose chromatography was applied and the column was fluted with the equilibration buffer. Fractions were collected and an aliquot of each was applied to endothelial cells. Fractions which inhibited endothelial proliferation were concentrated and dialyzed as above.

A SynChropak RPG (100×4.6 mm) column was equilibrated with $H_2O$/0.1% trifluoroacetic acid (TFA). HPLC-grade reagents (Pierce, Rockford, Ill.) were used. The sample from gel filtration chromatography was applied to the column and the column was fluted with a gradient of acetonitrile in 0.1% TFA at 0.5 ml/minute and fractions were collected. An aliquot of each was evaporated by vacuum centrifugation, resuspended in PBS, and applied to capillary endothelial cells. Inhibitory activity was further purified to apparent homogeneity by at least two subsequent cycles on the SynChropak C4 column.

To further characterize the 20 kDa inhibitor, it was tested on several cell lines of endothelial and non-endothelial origin. For the BCE assay, bovine capillary endothelial cells were obtained and grown as previously described (Folkman et al., 1979). For the proliferation assay, cells were washed with PBS and dispersed in a 0.05% solution of trypsin. A cell suspension (25,000 cells/ml) was made with DMEM+10% BCS+1% GPS, plated onto gelatinized 24-well culture plates (0.5 mewed), and incubated (37° C., 10% $CO_2$) for 24 hours. The media was replaced with 0.25 ml of DMEM+5% BCS+1% GPS and the test sample applied. After 20 minutes of incubation, media and bFGF were added to obtain a final volume of 0.5 ml of DMEM+5% BCS+1% GPS+1 ng/ml bFGF. After 72 hours, cells were dispersed in trypsin, resuspended in Hematall (Fisher Scientific, Pittsburgh, Pa.), and counted by Coulter counter.

Non-Endothelial Cell Proliferation Assays

Bovine aortic smooth muscle (SMC), bovine retinal pigment epithelial (RPE), mink lung epithelial (MLE), Lewis lung carcinoma (LLC), and EOMA cells and 3T3 fibroblasts were maintained in a 10% $CO_2$ and 37° C. incubator. For the proliferation assays, cells were washed with PBS and were dispersed in a 0.05% solution of trypsin. Optimal conditions for the cell proliferation assays were established for each different cell type. Fetal calf serum (FCS) was used for the RPE, MLE, and LLC cells and BCS was used for the other cell types. A cell suspension (20,000 cells/ml for SMC, RPE, MLE; 15,000 cells/ml for 3T3; 10,000 cells/ml for LLC, EOMA) was made with DMEM+10% bovine serum+1% GPS, plated onto 24-well culture plates (0.5 ml/well), and incubated (37° C., 10% CO2) for 24 hours. The media was replaced with 0.5 ml of DMEM+5% bovine serum+1% GPS and the test sample applied. After 72 hours, cells were dispersed in trypsin, resuspended in Hematall (Fisher Scientific, Pittsburgh, Pa.), and counted by Coulter counter.

Only endothelial cells were significantly inhibited, as shown in Table 2.

TABLE 2

EFFECT OF ENDOSTATIN PROTEIN ON ENDOTHELIAL AND NON-ENDOTHELIAL CELL PROLIFERATION

| INHIBITED | NON-INHIBITED |
|---|---|
| Bovine capillary endothelial cells | Bovine aortic smooth muscle cells |
| | Bovine retinal pigment epithelial cells |
| | 3T3 fibroblasts |
| | Mink lung epithelial cells |
| | EOMA hemangioendothelioma cells |
| | Lewis Lung carcinoma cells |

The inhibition was first observed at doses of 100 ng/ml with maximal inhibition observed at doses of 600 ng/ml or greater. No significant inhibition was seen for cells of non-endothelial origin at doses 1 log unit higher than those used to inhibit capillary endothelial cell proliferation (data not shown).

EXAMPLE 4

Microsequence Analysis of the 20 kDa Protein Reveals Identity to a Fragment of Collagen XVIII The 20 kDa inhibitor of capillary endothelial cell proliferation from the conditioned media was purified to homogeneity, as described in the above examples, resolved by SDS-PAGE, electroblotted onto PVDF (Bio-Rad, Richmond, Calif.), detected by Ponceau S stain, and excised from the membrane. N-terminal sequence was determined by automated Edman degradation on an PE/ABD Model 470A protein sequencer (Foster City, Calif.) operated with gas-phase delivery of trifluoracetic acid.

Sequence library searches and alignments were performed against combined GenBank, Brookhaven Protein, SWISS-PROT, and PIR databases. Searches were performed at the National Center for Biotechnology Information through the use of the BLAST network service.

Microsequence analysis of the inhibitor revealed identity to a C-terminal fragment of collagen XVIII. The molecular cloning and sequence of collagen XVIII was first described by Olsen and his coworkers and by Rehn and Pihlajaniemi (Oh et al., 1994; Rehn and Pihlajaniemi, 1994). Collagen XVIII is a novel collagen which consists of an N-terminal region with 3 splice variants (Muragaki et al., 1995; Rehn and Pihlajaniemi, 1995), a series of collagen-like domains with interruptions, and a 35 kDa C-terminal non-collagenous (NC1) domain. An 18-amino acid N-terminal microsequence analysis of the purified inhibitor of endothelial cell proliferation confirms that it is identical to a C-terminal fragment of this NC1 domain (FIG. 5). We have named this inhibitory fragment of collagen XVIII "endostatin protein" and it is included in the group of molecules that have endostatin protein activity.

EXAMPLE 5

Recombinant Mouse Endostatin Protein (Baculovirus or *E. coli*) Inhibits Endothelial Cell Proliferation in Vitro and Angiogenesis in Vivo The endothelial proliferation cell inhibitor of the present invention can be recombinantly expressed in any system used to express proteins. Non-limiting examples of such expressions systems include bacterial expression systems, yeast expression systems and insect viral expression systems.

Recombinant mouse endostatin protein was expressed using the BacPAK baculovirus expression system (CLONTECH Laboratories) following the manufacture's protocol. Briefly, a cDNA fragment encoding the signal sequence and C-terminal part (endostatin protein region) of mouse collagen XVIII was inserted into the pBacPAK8 transfer vector. BacPAK6 viral DNA (expression vector) and plasmid DNA of the pBacPAK8-endostatin protein clone (modified transfer vector) were then cotransfected into insect Sf21 cells and media containing expressed mouse endostatin protein was collected. The BacPAK6 was first digested with BSU36 enzyme to make it incompetent for independent replication. The media containing expressed mouse endostatin protein was applied to a 1.5×40 cm heparin Sepharose column which had been equilibrated with 50 mM NaCl 10 mM Tris pH 7.4. The column was washed with the equilibration buffer and was then eluted sequentially with 0.2 M NaCl, 0.4 M NaCl, 0.6 M NaCl, and 1 M NaCl in 10 mM Tris pH 7.4. All chromatography was performed at 4° C. The 0.6 M NaCl eluant (which inhibited bovine capillary endothelial cells in a 72 hour proliferation assay) was dialyzed (6–8000 MWCO) against PBS and then reapplied to the heparin Sepharose column. The column was eluted with a gradient of 50 mM NaCl—1.2 M NaCl in 10 mM Tris pH 7.4. An aliquot of each fraction was applied to bovine capillary endothelial cells as above and fractions which inhibited proliferation were pooled, dialyzed against PBS, and concentrated using a Nanospin Plus (Gelman Sciences) centrifugal concentrator (MWCO=10,000). SDS-PAGE of the concentrated sample revealed a discrete band of apparent $M_r$ of 20 kDa.

Expression and Purification of Recombinant Mouse Endostatin Protein from *E. coli*

The C-terminal part of the cDNA of collagen XVIII was used to amplify the cDNA of mouse endostatin protein which was cloned into the pETKH1 vector (pET11d derivative) (Studier et al., 1990). Induction resulted in the production of a fusion protein carrying the amino acid sequence MARRASVGTD (SEQ ID NO:3) (RRAS=protein kinase A recognition sequence) and 6 histidine residues at the N-terminus followed by the sequence of mouse endostatin protein (pTB01#8). The pTB01#8 plasmid was transformed into BL21:DE3 and the fusion protein was purified on $Ni^{+2}$-NTA-beads as described (QiaExpressionist Handbook, Qiagen). Briefly, *E. coli* were grown until an $O.D._{600}$ of 0.8–0.9 and expression of the fusion protein was then induced for 3 hours with 1 mM IPTG. The bacteria were pelleted and resuspended in 8 M urea, 10 mM Tris-HCl pH 8.0 containing 10 mM imidazole and incubated for 1 hour at room temperature. The suspension was centrifuged for 15 minutes at 20,000 g and the supernatant incubated with the $Ni^{+2}$-NTA beads for 1 hour at room temperature. The suspension was transferred into a column and washed with 8 M urea, 0.1 M Na-phosphate, 10 mM Tris-HCl pH 6.25 containing 10 mM imidazole. The protein was eluted with the same buffer containing 250 mM imidazole. The fractions containing endostatin protein were extensively dialyzed against PBS. During dialysis, the endostatin protein precipitated. The precipitated endostatin protein was resuspended in PBS, the protein concentration was adjusted to 2–4 mg/ml, and the endostatin protein was stored at −20° C. until use. For the mouse studies, endostatin protein was delivered as a suspension in PBS. For the chick chorioallantoic assay, endostatin protein was further dialyzed against water and then lyophilized.

Recombinant mouse endostatin protein was produced in both baculovirus and *E. coli* expression systems. Using sequential heparin Sepharose chromatography, recombinant mouse endostatin protein was purified to apparent homogeneity from insect cell media. $Ni^{+2}$-NTA-agarose was used to purify the *E. coli*-derived mouse endostatin protein.

SDS-PAGE revealed a discrete band of approximately 20 kDa or approximately 22 kDa (reduced) purified to apparent homogeneity for baculovirus and *E. coli*-derived recombinant endostatin proteins, respectively (data not shown). Both were dialyzed against PBS prior to use. After dialysis, the material from the *E. coli* system precipitated and was delivered as a suspension for subsequent in vivo studies. Recombinant endostatin protein from baculovirus specifically inhibited the proliferation of bovine capillary endothelial cells in a dose-dependent fashion. The inhibition was seen at doses of 100 ng/ml with maximal inhibition observed at doses above 600 ng/ml. No significant inhibition of proliferation of cells of non-endothelial origin or of the EOMA cells was observed when endostatin protein was tested at doses up to 1 log unit higher than those used to inhibit endothelial cell proliferation.

The precipitated (un-refolded) material was not testable in vitro, because of its insolubility. However, a small percentage was soluble in PBS during dialysis and this fraction was used for the endothelial cell assays. Furthermore, after refolding, it was soluble and inhibited endothelial proliferation (data not shown). When this soluble material was applied to endothelial cells, it was found to be inhibitory at concentrations comparable to both the native and baculovirus-derived endostatin protein.

To test for the ability of recombinant mouse endostatin protein to inhibit in vivo angiogenesis, we used the chick chorioallantoic membrane (CAM) assay (Folkman, 1985; Nguyen et al., 1994 which are incorporated herein by reference). Briefly, three day old fertilized white Leghorn eggs (Spafas, Norwich, Conn.) were cracked, and embryos with intact yolks were placed in 100×20 mm petri dishes (Folkman, 1985). After 3 days of incubation (37° C. and 3% $CO_2$), a methylcellulose (Fisher Scientific, Fair Lawn, N.J.) disc containing endostatin protein was applied to the CAM of individual embryos. The discs were made by desiccation of endostatin protein in 10 µl of 0.45% methylcellulose (in $H_2O$) on teflon rods. After 48 hours of incubation, embryos and CAMs were observed by means of a stereomicroscope.

At doses of 10–20 µg/10 µl disc, there was potent inhibition of in vivo angiogenesis for both the *E. coli* and the baculovirus-derived endostatin proteins in all of the tested CAMs (n=5/group). The *E. coli* derived-endostatin protein precipitate gradually dissolved over 5 days and produced a sustained antiangiogenic effect on the implanted CAMs. In contrast, the soluble baculovirus-derived endostatin protein dissolved within 24 hours and gave a maximal antiangiogenic effect within a period of 48 hours. There was no evidence of toxicity in any of the chick embryos tested.

Human endostatin protein was produced recombinantly using similar methods.

EXAMPLE 6

Recombinant Mouse Endostatin Protein Inhibits the Growth of Metastases

Because tumor growth is angiogenesis dependent, we treated Lewis lung carcinoma metastases systematically with recombinant mouse endostatin protein expressed in the baculovirus system. Animals with Lewis lung carcinomas of 600–1200 $mm^3$ tumors were sacrificed and the skin overlying the tumor was cleaned with betadine and ethanol. In a laminar flow hood, tumor tissue was excised under aseptic conditions. A suspension of tumor cells in 0.9% normal saline was made by passage of viable tumor tissue through a sieve and a series of sequentially smaller hypodermic needles of diameter 22- to 30-gauge. The final concentration was adjusted to 1×107 cells/ml and the suspension was placed on ice. After the site was cleaned with ethanol, the subcutaneous dorsa of mice in the proximal midline were injected with 1×106 cells in 0.1 ml of saline.

When tumors were 1500 $mm^3$ in size, approximately 14 days after implant, the mice underwent surgical removal of the tumor. The incision was closed with simple interrupted sutures. From the day of operation, mice received daily intraperitoneal injections of recombinant (baculovirus) mouse endostatin protein or saline. Mice received 0.3 mg/kg/day of endostatin protein once daily via subcutaneous injection. When the control mice became sick from metastatic disease (i.e., after 13 days of treatment), all mice were sacrificed and autopsied. Lung surface metastases were counted by means of a stereomicroscope at 4× magnification.

The growth of Lewis lung carcinoma metastases was almost completely suppressed by the systemic administration of endostatin protein at a dose of 0.3 mg/kg/day given subcutaneously (7±3 metastases/mouse, n=4, $p<0.001$). In contrast, in mice treated with saline after removal of a Lewis lung carcinoma primary tumor, lung metastases grew rapidly (77±7 metastases/mouse). Lung weight, which reflects tumor burden, was 240±25 mg in the endostatin protein treated mice versus 760±30 mg in the control mice ($p<0.001$). Further, there was no weight loss or evidence of toxicity in any of the mice treated with endostatin protein.

EXAMPLE 7

Recombinant Mouse Endostatin Protein Inhibits the Growth of Primary Tumors

The yield of endostatin protein from the baculovirus system was lower than that of the *E. coli* system, i.e. 1–2 mg/liter versus 30–40 mg/liter. Therefore, *E. coli*-derived endostatin protein was used to study the effect of endostatin protein therapy on primary tumor growth. Recombinant mouse endostatin protein was produced from *E. coli* in sufficient quantity to treat Lewis lung carcinoma primary tumors. The endostatin protein was administered as a suspension of the precipitated purified protein to mice bearing Lewis lung carcinomas of at least 100–200 $mm^3$. The protein was purified by conventional means but was not refolded prior to its administration to the mice. The injected precipitate was slowly resorbed over 24–48 hours.

We are unaware of any precedent for the use of an injected depot of non-refolded recombinant protein as a sustained-release method in animals. Nevertheless, endostatin protein gradually resorbed in vivo and proved to have potent anti-angiogenic activity which resulted in prolonged anti-tumor and antiangiogenic activity. Therefore, these data suggest a novel general method for the controlled release of recombinant proteins. Based on this rationale, we have delivered non-refolded recombinant angiostatin protein from *E. coli* with similar success.

Accordingly, an aspect of the invention is the administration of recombinant endostatin protein or endostatin protein analogs in an un-refolded state so as to provide a sustained release depot of endothelial cell proliferation inhibiting protein over a period of at least 8 hours, desirably at least 12 hours, more desirably at least 24 hours or at least 48 hours, depending on the patient and the disease to be treated. Optionally recombinant and un-refolded angiostatin protein is administered to similarly provide a sustained release depot of protein capable of releasing angiostatin protein over a period of at least 8 hours, desirably at least 12 hours, more desirably at least 24 hours or at least 48 hours, depending on the patient and the disease to be treated.

Mice were implanted with Lewis lung carcinomas as described above. Tumors were measured with a dial-caliper and tumor volumes were determined using the formula width$^2$×length×0.52, and the ratio of treated to control tumor volume (T/C) was determined for the last time point. After tumor volume was 100–200 mm$^3$ (0.5–1% of body weight), which occurred within 3–7 days, mice were randomized into two groups. One group received recombinant mouse endostatin protein (*E. coli*) as a suspension in PBS injected subcutaneously at a site distant from the tumor once daily. The other group received comparable injections of the vehicle alone. The experiments were terminated and mice were sacrificed and autopsied when the control mice began to die.

The growth of Lewis lung primary tumors was potently suppressed by systemic therapy with endostatin protein. Increasing the dose of endostatin protein was associated with improved efficacy (data not shown). At a dose of 10 mg/kg, tumor growth was inhibited by 97% as compared to control mice treated with vehicle alone. At a dose of 20 mg/kg given once daily, in two separate experiments, there was an almost complete regression of established primary tumors (>99% inhibition, p<0.001). These surprising and unexpected results are shown in FIGS. 6 and 7.

FIGS. 8, 9, 10 and 11 demonstrate the effectiveness of recombinant mouse endostatin protein for inhibiting tumor growth in a variety of different tumor models. Also demonstrated is the effectiveness of endostatin protein derived from human for inhibiting tumor growth.

Immunohistochemical analysis (FIG. 12) of the residual small tumors showed a potent inhibition of angiogenesis in the endostatin protein treated tumors. Further, the proliferative index of tumors in the endostatin protein and saline treated mice was at the same high level in both groups while the apoptotic index increased 8-fold after endostatin protein therapy. Thus, endostatin protein therapy results in a similar pattern of tumor dormancy to the one we have previously described for angiostatin protein (Holmgren et al., 1995; O'Reilly et al., 1996). Further, there was no evidence of drug-related toxicity in any of the treated mice.

After discontinuation of endostatin protein therapy, a tumor recurred at the primary site within 5–14 days, became vascularized, and eventually killed the mice (data not shown). Notably, we found that *E. coli*-derived recombinant mouse endostatin protein with a C-terminal polyhistidine tag, which was expressed. purified and administered in a comparable fashion to the N-terminal tagged product described above did not inhibit angiogenesis in the CAM assay and had no effect on the growth of Lewis lung carcinomas (data not shown). These data argue strongly that the anti-tumor and antiangiogenic activity of recombinant endostatin protein are due to the specific structure of endostatin protein and not to a contaminant in the sample.

FIG. 13 shows the results of cycled treatment of Lewis lung carcinoma with recombinant mouse endostatin protein derived from *E. coli*. These results clearly show reproducible endostatin protein-dependent regression of tumor mass, followed by tumor growth after termination of endostatin protein treatment.

These results show that a murine hemangioendothelioma produces a novel and specific 20 kDa inhibitor of endothelial cell proliferation in vitro which is also a potent inhibitor of angiogenesis and tumor growth in vivo. The N-terminal sequence of this inhibitor, endostatin protein, is identical to a C-terminal fragment of collagen XVIII. Systemic administration of recombinant endostatin protein potently inhibits angiogenesis, maintains metastases at a microscopic size, and regresses primary tumors to less than 1 mm$^3$, a reduction of over 150-fold. For as long as mice are treated there is no regrowth of tumors, no evidence of drug resistance, and no toxicity. It is interesting to note that some fragments of the C-terminal domain of collagen type XVIII that are longer than endostatin protein do not inhibit endothelial cell proliferation (data not shown).

Endostatin protein was discovered by the same strategy employed to find angiostatin protein (O'Reilly et al., 1994), i.e., isolation from a tumor. While it is counter-intuitive that tumors should be a source of angiogenesis inhibitors, the results reported here seem to validate this approach.

This leads to the question of why angiogenesis inhibitors should be present in tumors that are angiogenic. One possibility is that an inhibitor could be 'left-over' after downregulation of its production by a tumor cell undergoing the switch to the angiogenic phenotype. This appears to be the case for thrombospondin produced by Li-Fraumeni cells in which the second allele for p53 is mutated or deleted (Dameron et al., 1994).

A second possibility is that the proteolytic activity which accompanies tumor growth, and which is an important component of capillary blood vessel growth, may also mobilize circulating angiogenesis inhibitors from precursor proteins which are not inhibitory themselves. Angiostatin protein for example, inhibits angiogenesis and endothelial cell proliferation while plasminogen does not (O'Reilly et al., 1996; O'Reilly et al., 1994). For endostatin protein, a similar pattern is revealed.

Histology of tumors which regressed under endostatin protein therapy showed perivascular cuffing of tumor cells surrounding one or more microvessels in which angiogenesis was blocked. Tumor cells displayed high proliferation balanced by high apoptosis, with no net gain in tumor size. These data are consistent with a model of a new type of tumor dormancy recently proposed (Holmgren et al., 1995). Furthermore, endostatin protein inhibited proliferation of endothelial cells in vitro, but had no effect on Lewis lung carcinoma cells, or other cell types including smooth muscle, epithelium, fibroblasts, and the EOMA cell line from which it was purified.

The fact that a specific inhibitor of endothelial cell proliferation can regress a tumor to a microscopic size and hold it in a dormant state, despite the fact that the tumor cells are refractory to the inhibitor from the outset, indicates that the endothelial population can exert powerful growth regulatory control over the tumor cells.

The results with endostatin protein support the theory (Folkman, 1996) that for therapeutic purposes, it is fruitful to think about a tumor in terms of two distinct cell populations: a tumor cell population and an endothelial cell population, each of which can stimulate growth of the other. Growth of each cell population may be optimally inhibited by agents which selectively or specifically target that cell type, i.e., cytotoxic chemotherapy and antiangiogenic therapy. Furthermore, combined treatment of both cell populations may be better than treatment of either cell type alone.

To test this theory mice seeded with Lewis lung carcinomas, and bearing tumors which had attained a size of approximately 300 mm³, were treated with a combination therapy comprising angiostatin protein and endostatin protein, each at a dose of 20 mg/kg/day for 25 days. Tumors regressed to microscopic levels by about day 10 of treatment. A completely unexpected finding was that tumors remained regressed and dormant for approximately three months, even after all treatment was terminated, as is shown in FIG. 14. Experiments of longer duration indicate that an initial treatment of tumor with a combination of angiostatin protein and endostatin protein causes a very long term dormancy, the actual period of which is unknown at this time.

Such long term dormancy is considered a cure to one skilled in the art. For example, the NIH guideline for determining when a treatment is effective as a cancer cure, is that the tumor remain dormant (i.e. not increasing in size) for ten times the normal doubling time of the tumor. The dormancy length achieved using a combination of endostatin protein and angiostatin protein far exceeds this criteria.

Accordingly, an important aspect of the invention is a composition comprising a combination of angiostatin protein and endostatin protein, or an endostatin protein analog, in amounts sufficient to cause long term dormancy, or cure, of angiogenesis-dependent cancers when administered to patients with angiogenesis-dependent cancers. Administration can be systemically, for example by injection, in which case the dosage is determined depending upon the patient and the particular cancer, but which generally is at least 0.2 mg/kg/day, desirably at least 2.0 mg/kg/day, more desirably at least 20 mg/kg/day. Generally, the composition is administered daily for at least 10 days, desirably at least 20 days, more desirably at least 25 days. Alternative systemic administration routes include, orally where the composition is formulated, for example into coated microbeads, to protect the protein from inactivating digestive environments; transdermally; and via pump.

Alternatively, different dosages and treatment periods can be used if the composition is administered locally to an angiogenesis-dependent site, such as a tumor. Such administration may be, for example, surgical implantation or local injection into, or near by, the site.

EXAMPLE 8

Isolation of the Putative Receptor for Endostatin Protein.

Both endostatin protein and angiostatin protein appear to be specific inhibitors of endothelial cell proliferation. Therefore, it is likely that endostatin protein binds to specific structures exclusively expressed on the surface of endothelial cells. We are not aware of the existence of any other specific inhibitors of endothelial cell proliferation.

Identifying and isolating proteins which specifically bind to endostatin protein is accompanied by methods well known in the art, for example by affinity chromatography and expression cloning.

Affinity chromatography. Bovine Capillary Endothelial cells (BCE) are radiolabeled with [³⁵S]-methionine, total cell and membrane extracts prepared and applied to affinity columns prepared with endostatin protein. As a negative control, fibroblast protein extracts are isolated in a similar way. Bound proteins are eluted from the column using a NaCl gradient and the different fractions are analyzed using standard SDS-PAGE and autoradiography. This procedure yields proteins that are tightly bound to the endostatin protein column and present only in the endothelial cell derived fractions. Comparing the gel electrophoretic patterns of the two cell types reveals expressed proteins unique to the BCE cells. Protein sequences subsequently are determined and corresponding gene(s) cloned. A cDNA library of bovine capillary endothelial cells, is prepared and screened with a degenerative oligo based PCR technique to locate the cDNA(s) of the endostatin protein-specific binding rotein(s). Hybridization using degenerative oligonucleotides to the corresponding cDNA, is also used to identify genes of endostatin protein binding proteins. Another approach is to raise antibodies against the peptide sequences with methods described earlier in the Detailed Description and immuno-screen the same library.

Expression cloning. A cDNA library of BCE cells is prepared. Poly-A mRNA is isolated from BCE cells whose proliferation has previously been inhibited by endostatin protein. These cells express an endostatin protein binding protein. The corresponding cDNA library is transfected into cells allowing high expression of the various cDNAs. Binding activity of endostatin protein to cells which express the receptor protein on the surface is used as a positive selection of these cells. To select for these cells, purified endostatin protein is labeled with biotin and consequently detected using either streptavidin coupled magnetic-beads or FACS sorting. Alternatively, an antibody against endostatin protein is used for screening. After selection of the positive cells, the corresponding plasmids are isolated, amplified and transfected again into high expression cells. After several rounds of positive selection, plasmids are analyzed for identical inserts using endonuclease digestion and PCR. Using these data, complementation groups are formed, sequenced and analyzed with the BLAST network program. In addition to computer analysis, individual cDNAs are re-transfected into high expression cells and tested for endostatin protein binding activity under different conditions (e.g., competition with non-labeled endostatin protein, time-course of binding, Scatchard analysis, etc. in other words the use of "classical" receptor characterization procedures known to those skilled in the art).

EXAMPLE 9

Determination of the Minimal Region of the Mouse Endostatin Protein Responsible for its Antiangiogenic Activity.

Different PCR primers are designed, the corresponding cDNAs cloned into the *E. coli* expression system, and the different endostatin protein fragments purified to homogeneity. The full length cDNA is cut from both the N- and C-terminus. As a first screen the capillary endothelial proliferation assay and the chick embryo assay are used to determine the residual activity compared to the full length fragment.

EXAMPLE 10

Determination of the Putative Enzyme(s) which may Release Endostatin Protein from Collagen XVIII Collagen XVIII belongs to the non-fibrillar collagen type family and can be found in three different splicing variants encoding for proteins with 1315-, 1527-, and 1774 amino acid residues (Rehn, *PNAS* 91:4234, 1994). The difference is caused by alterations in the N-terminal part of the gene and therefore all three splicing variants could potentially be the source of endostatin protein which itself is a fragment of the non-collagenous domain 11 (NC11). The function of collagen XVIII is not known, but because its message is substantially expressed in highly vascularized organs, a role in perivascular matrix assembly and/or structure has been proposed (Oh, et al., *Genomics,* 19:494, 1994). A first clue about the function of collagen XVIII came from the purification of endostatin protein as a potent inhibitor of endothelial cell proliferation.

From this preliminary data and from our initial observation that endostatin protein was purified from conditioned medium of a hemangioendothelioma (EOMA), we asked whether the enzyme(s) which release endostatin protein from collagen XVIII could be identified?

The last 325 amino acid residues, encoding for the NC11 domain, are expressed in *E. coli* and the insect cell baculovirus system, the purified protein is used as a substrate to identify enzymes that clone this region of collagen XVIII. By PCR, a cDNA fragment encoding the NC11 domain is cloned into an *E. coli* expression vector (pET series) which allows high expression of the target protein after induction with IPTG. Alternatively, a vector suitable for insect cell expression is used. The proteins are tagged with the $HIS_6$-Tag located on the C-terminus for purification using $Ni^{2+}$-NTA-beads. An $Ni^{2+}$-NTA-alkaline phosphatase conjugate can detect the C-terminus by Western blotting. Another construct is made which not only has a $HIS_6$-Tag on the C-terminus, but will also encode the hemagglutinin (HA-tag on the N-terminus. This is detected by Western blotting with an HA-specific monoclonal antibody. The N- and C-terminus of the protein followed after incubation with EOMA supernatant and different metalloproteinase extracts.

Cleavage product is detected by SDS-PAGE analysis or Western blotting, the protein is re-purified using the $Ni^{2+}$-NTA beads, eluted with imidazole, dialyzed against PBS and tested for inhibitor activity in the various in vitro and in vivo assays (e.g., endothelial cell proliferation, chick embryo, and mouse corneal assay). If the purified cleavage product shows inhibitory activity, N-terminal amino acid sequencing is performed and compared to the original starting sequence of endostatin protein obtained from the EOMA supernatant. Accordingly, the cleavage procedure can be scaled up to purify sufficient protein for testing in tumor-bearing mice, and to compare this activity to that of the full length NC11 domain.

EXAMPLE 11

Production of Monoclonal Endostatin Protein Antibodies

This example pertains to the production of monoclonal endostatin protein antibodies, which was assisted by Multiple Peptide Systems (San Diego, Calif.). One group of five female Balb/c mice were immunized according to the procedures described below with a synthetic human endostatin protein peptide of the sequence:

CKDELLFPSWEALFSGSEGPLKPGAR (SEQ ID NO:2).

Sera were collected from immunized mice and analyzed for the presence of endostatin protein-specific antibodies. A mouse was selected for use in hybridoma development based on these results.

Preparation of Peptides for use in Immunization 3 mg of purified endostatin protein peptide were coupled through the terminal cysteine thiol to Keyhole Limpet Hemocyanin (KLH) with the heterobifunctional cross-linking agent Maleimidobenzoyl-N hydroxysuccinimide ester (MBS), in a ratio of 1 part endostatin protein peptide to 1 part KLH (w/w).

Preparation of Peptides for use in ELISA Tests 3 mg of purified endostatin protein peptide were coupled through the terminal cysteine thiol to Bovine Serum Albumin (BSA) with the heterobifunctional cross-linking agent Maleimidobenzoyl-N hydroxysuccinimide ester (MBS), in a ratio of 1 part endostatin protein peptide to 1 part BSA (w/w).

For primary immunization, the antigen was suspended in PBS Buffer, emulsified by mixing with an equal volume of Complete Freund's Adjuvant (CFA) and injected intraperitoneally into the mice. Subsequent immunizations were performed using Incomplete Freund's Adjuvant (ICFA) or no adjuvant.

Immunization Schedule

| Day | Immunization |
| --- | --- |
| 0 | Primary Immunization<br>Each mouse received 50 µg peptide-KLH in Complete Freund's Adjuvant, intraperitoneally. Mice rested for four weeks. |
| 28 | First Boost (2nd immunization)<br>Each mouse received 25 1 µg peptide-KLH in Incomplete Freund's Adjuvant intraperitoneally. |
| 42 | 2nd boost (3rd immunization)<br>Each mouse received 10 µg peptide-KLH in phosphate-buffered saline (PBS). |
| 49 | 1st bleed and analysis |
| 56 | 3rd boost (4th immunization)<br>Each mouse received 5 µg peptide-KLH in PBS. |
| 63 | 2nd bleed and analysis |
| 70 | 4th boost (5th immunization)<br>Each mouse received 5 µg peptide-KLH in PBS. |
| 77 | 3rd bleed and analysis |

ELISA

Microtiter wells of IMMULON II™ plates were coated with the free endostatin protein peptide or endostatin protein peptide-BSA at 1 µg/ml in 50 mM carbonate buffer, pH 9.6. Plates were sealed and incubated overnight at room temperature. The next day, liquid was removed from all wells, and the wells were blocked for 30 min. with 30% BSA-PBS-0.05% TWEEN™. The blocking solution was removed and serial dilutions of mouse sera in this buffer were added (50 µl/well) for 30 min. at room temperature with agitation. Wells were washed 3× with PBS-0.05% TWEEN™. A 1:1000 dilution of HRP—conjugated goat anti-mouse IgG/IgA/IgM (American Qualex) was added to each well (50 pl/well) for 30 min. at room temperature with agitation. Wells were washed 3× with PBS 0.05% TWEEN™. Each well received 200 μl of ortho-Phenylenediamine (OPD) substrate for 30 min. at room temperature (50 ml OPD substrate buffer: 20 mM sodium phosphate, 300 μl 30% $H_2O_2$, 20 mg OPD). Wells were quenched with addition of 3M HCl, and O.D.'s were read at dual wavelengths (490nm–650 nm). Results are expressed by the reciprocal of the serum dilution that results in an $OD_{490}$ of 0.1.

ELISA Test Results

| Mouse # | Against BSA conjugate 1st Bleed Titer | Against BSA conjugate 2nd Bleed Titer | Against BSA conjugate 3rd Bleed Titer | Against Free Peptide 1st Bleed Titer | Against Free Peptide 2nd Bleed Titer | Against Free Peptide 3rd Bleed Titer |
|---|---|---|---|---|---|---|
| 1 | 200 | 12,800 | 25,600 | 400 | 6,400 | 12,800 |
| 2 | 400 | 1,600 | 6,400 | 400 | 1,600 | 3,200 |
| 3 | 400 | 3,200 | 6,400 | 800 | 3,200 | 3,200 |
| 4 | 800 | 12,800 | 12,800 | 400 | 3,200 | 3,200 |
| 5 | Died Day 48 | Died Day 48 | Died Day 48 | Died Day 48 | Died Day 48 | Died Day 48 |

Based upon the above results, Mouse #1 was selected as the fusion mouse and Mouse #4 was designated as the backup fusion mouse.

Production of Hybridomas

This example was conducted in order to make and analyze initial hybridomas produced by the fusion of spleen cells from mice immunized above, and a myeloma cell line.

Mice #1 and #4 were both administered a pre-fusion booster injection on Day 83. Three days later, spleen cells from Mouse #1 were fused with two different myeloma cell lines and seeded into 96-well plates, three plates per myeloma cell lines. The two myeloma cell lines used were designated FO and P3X63Ag8.1 (Ag1).

Two weeks after fusion, hybridoma cultures were tested in ELISA for reactivity against the endostatin protein peptide-BSA conjugate. Six positive parental hybridomas were identified and expanded in volume. Once expanded, the 6 positive parental hybridomas were ELISA tested again for reactivity with the peptide-BSA conjugate. Two parental cultures remained positive. One reacted very strongly (Culture No. 2001) while the other was only weakly positive (Culture No. 2002). These two cultures were selected for subcloning.

Subcloning of Parental Hybridoma Cultures and Ascites Production from Final Subclones Two parental hybridomas, Culture Nos. 2001 and 2002, were cloned by limiting dilution. A total of twenty-three (23) positive subclones were identified and expanded. All of these subclones came from parental hybridoma Culture No. 2001 and reacted in ELISA with the endostatin protein peptide-BSA conjugate and with human endostatin protein. Samples of 18 subclones that had grown sufficiently for samples to be harvested were further analyzed. All of the samples detected human endostatin protein in Western Blot analysis. None of the clones cross-reacted with mouse endostatin protein or collagen XV (data not shown).

Based on the ELISA data, the five (5) "best" subclones were selected for ascites production. Subclones were injected for ascites production on day 171 and production was completed 14 days later.

Characterization OF MAB96-2 Monoclonal Antibody Ascites

| Clone No. | Ascites Volume (ml) | ELISA Titer (Peptide-BSA Conj.) | Ig subtype | Ig mg/ml |
|---|---|---|---|---|
| 2001.23 | 29 | 12,800 | IgG2a | 18.7 |
| 2001.24 | 26 | 25,600 | IgG2a | 15.3 |
| 2001.27 | 20 | 12,800 | IgG2a | 44.3 |
| 2001.31 | 16 | 51,200 | IgG2a | 20.9 |
| 2001.32 | 16 | 25,600 | IgG2a | 30.2 |

The two positive parental hybridomas (2 vials each), the five subclones (4 vials each) selected for ascites production and twelve positive subclones (2 vials each) selected as backup for ascites production were frozen in liquid nitrogen.

Analysis

Western Blotting analysis revealed that of the 1/1,000–1/5,000 dilution, monoclonal antibodies from ascites from 2001.31 recognize human endostatin protein recombinantly produced from E. coli (FIG. 15.A, lane 1) and NIH 3T3 cells expressing human endostatin protein (data not shown). These particular antibodies showed no cross-reactivity to mouse endostatin protein produced in E. coli, or Pichia pastoris yeast cells (data not shown), nor a cross-reactivity to mouse collagen XV produced in E. coli (data not shown).

The antibody was shown to be operable for an ELISA, and can also work for immunoprecipitation assays. For immunofluorescence, the cells were fixed with ice-cold 100% methanol for 10 min. on ice. The working dilution was 1/5,000–1/20,000 (non purified ascites) and the bound antibodies were detected using anti-mouse-biotin and avidin-FITC (VECTOR).

The monoclonal antibody does not recognize the collagen XVIII network produced by human dermal microvascular endothelial cells, but shows an intracellular staining which overlaps with staining obtained with a polyclonal antibody against the N-terminus of collagen XVIII. The monoclonal antibody may not recognize endostatin protein when it is not cleaved off from collagen XVIII. This could mean that the antibody is specific for endostatin protein and longer fragments which are released from collagen XVIII during matrix remodeling.

EXAMPLE 12

Production of Polyclonal Endostatin Protein Antibodies

This example pertains to the production of polyclonal endostatin protein antibodies, performed at Children's Hospital (Boston, Mass.).

Expression and Purification of Recombinant Mouse Endostatin Protein from E. Coli The C-terminal part of the cDNA of collagen XVIII was used to amplify the cDNA of mouse endostatin protein that was cloned into the pETKH1 vector (pET11d derivative) (Studier, et al. (1990) Use of T7 RNA polymerase to direct expression of cloned genes. *Methods Enzymol.* 85:60–89; See generally, Oh, et al. (1994) Isolation and sequencing of cDNAs for proteins with multiple domains of Gly-Xaa-Yaa repeats identify a distinct family of collagenous proteins. *Proc. Natl. Acad. Sci. USA* 91, 4229–4233; Rehn, et al. (1994). α1(XVIII), a collagen chain with frequent interruptions in the collagenous sequence, a distinct tissue distribution, and homology with type XV collagen. *Proc. Natl. Acad. Sci. USA* 91, 4234–4238, all of which are incorporated by reference in their entirities).

Induction resulted in the production of a fusion protein carrying the amino acid sequence MARRASVGTD (SEQ ID NO:3) (RRAS (SEQ ID NO:4)=protein kinase A recognition sequence) and six histidine residues at the N-terminus followed by the sequence of mouse endostatin protein (pTB01#8). The pTB01#8 plasmid was transformed into BL21:DE3 and the fusion protein was purified on $Ni^{2+}=$NTA-beads as described (QiaExpressionist Handbook, Qiagen). In brief, *E. coli* were grown until an $OD_{600}$ of 0.8–0.9 and expression of the fusion protein was then induced for 3 hr with 1 mM IPTG. The bacteria were pelleted and resuspended in 8 M urea, 10 mM Tris-HCl (pH 8.0) containing 19 mM imidazole, and incubated for 1 hr at room temperature. The suspension was centrifuged for 15 min. at 20,000 g and the supernatant incubated with the $Ni^{2+}$=NTA-beads for 1 hr at room temperature. The suspension was transferred into a column and washed with 8 M urea, 0.1 M Na-phosphate, 10 mM imidazole, 10 mM Tris-HCl (pH 8.0) followed by the same buffer (pH 6.25). The protein was eluted with the pH 6.25 buffer containing 250 mM imidazole.

Six rabbits (A–F) were immunized by standard procedures with mouse endostatin protein produced in *E. coli*. The first two immunizations were performed with endostatin protein cut from a gel. Further immunizations were performed with endostatin protein combined with Incomplete Freund's Adjuvant (ICFA). The dose was approximately 500 µg/rabbit.

Immunization Protocol—Rabbits A–F. 28706

| Day | Bleed | Ser Vol | Adjuvant | Route | Inj Vol |
|---|---|---|---|---|---|
| 0 | Pre-Immune Bleed | 10 | | | |
| 44 | IMMUNIZATION | | CFA | ID | 1.0 |
| 68 | IMMUNIZATION | | GEL | IM | 1.0 |
| 79 | Test Bleed | 10 | | | |
| 97 | IMMUNIZATION | | ICFA | IM | 1.0 |
| 107 | Test Bleed | 10 | | | |
| 124 | IMMUNIZATION | | ICFA | IM | 1.0 |
| 135 | Test Bleed | 10 | | | |
| 143 | Test Bleed | 10 | | | |
| 167 | IMMUNIZATION | | ICFA | IM | 1.0 |
| 178 | Test Bleed | 10 | | | |
| 210 | IMMUNIZATION | | ICFA | IM | 1.0 |
| 220 | Test Bleed | 10 | | | |
| 230 | Test Bleed | 10 | | | |
| 272 | IMMUNIZATION | | ICFA | IM | 1.0 |
| 284 | Production Bleed | 20 | | | |
| 311 | Production Bleed | 20 | | | |

Analysis:

Analysis of the antibody reactivity using western blotting techniques, revealed that the polyclonal antibodies produced in rabbits recognized both mouse endostatin protein (See FIG. 15.B, lane 2; FIGS. 16.A, 16.B; and FIGS. 17.A and 17.B, middle (+) lanes) and human endostatin protein (See FIG. 15.B, lane 1; FIGS. 17.A and 17.B, right (+) lanes; and FIG. 18, first 3 lanes). These antibodies also recognize the endostatin protein homologous region of mouse collagen XV, which is 65% identical, to endostatin protein/collagen XVIII (See FIG. 15.B, lane 3; and FIG. 18, last 3 lanes). The antibodies also recognized mouse and human endostatin protein expressed in yeast and mammalian cell culture systems (data not shown). Use of beta-mercaptoethanol in the SDS sample buffer, improved recognition of protein by antibodies (data not shown). Working dilutions of approximately 1/1,000–1/5,000 using ECL system were used.

Immunofluorescence assays revealed substantial matrix staining of collagen XVIII using human dermal microvascular endothelial cells (data not shown). However, intracellular staining was less significant. Working dilution was 1/500 of rabbit F serum (3rd boost). Cells were fixed with 100% methanol on ice for 10 min. and the antibodies were detected using either anti-rabbit-biotin and avidin-FITC (VECTOR) or anti-rabbit-TEXAS RED (VECTOR).

REFERENCES

The following references are hereby incorporated by reference herein in their entirety.

Angiolillo, A. L., Sgadari, C., Taub, D. D., Liao, F., Farber, J. M., Miaheshwari, S., Kleinman, H. K., Reaman, G. H., and Tosato, G. (1995). Human interferon-inducible protein 10 is a potent inhibitor of angiogenesis in vivo. J. Exp. Med. 182, 155–162.

Cao, Y., Chen, C., Weatherbee, J. A., Tsang, M., and Folkman, J. (1995). Gro-beta, a C-X-C chemokine, is an angiogenesis inhibitor that suppresses the growth of Lewis lung carcinoma in mice. J. Exp. Med. 182, 2069–2077.

Chen, C., Parangi, S., Tolentino, M. J., and Folkman, J. (1995). A strategy to discover circulating angiogenesis inhibitors generated by human tumors. Cancer Res. 55, 4230–4233.

Clapp, C., Martial, J. A., Guzman, R. C., Rentier-Delrue, F., and Weiner, R. 1. (1993). The 16-kilodalton N-terminal fragment of human prolactin is a potent inhibitor of angiogenesis. Endocrinology 133, 1292–1299.

Dameron, K. M., Volpert, O. V., Tainsky, M. A., and Bouck, N. (1994). Control of angiogenesis in fibroblasts by p53 regulation of thrombospondin-1. Science 265, 1582.

Folkman, J. (1996). Tumor angiogenesis and tissue factor. Nature Med. 2, 167–168.

Folkman, J. (1989). What is the evidence that tumors are angiogenesis dependent?. J. Natl. Cancer Inst. 82, 4–6.

Folkman, J. (1985). Angiogenesis and its inhibitors. In Important Advances in Oncology 1985, V. T. DeVita, S. Hellman, and S. Rosenberg, eds. (Philadelphia: J.B. Lippincott Company), pp. 42–62.

Folkman, J., Haundenschild, C. C., and Zetter, B. R. (1979). Long-term culture of capillary endothelial cells. Proc. Natl. Acad. Sci. USA 76, 5217–5221.

Gavrieli, Y., Sherman, Y., and Ben-Sasson, S. A. (1992). Identification of programmed cell death in situ via specific labeling of nuclear DNA fragmentation. J. Cell Biol. 119, 493–501.

Good, D. J., Polyerini, P. J., Rastinejad, F., Le Beau, M. M., Lemons, R. S., Frazier, W. A., and Bouck, N. P. (1990). A tumor suppressor-dependent inhibitor of angiogenesis is immunologically and functionally indistinguishable from a fragment of thrombospondin. Proc. Nat. Acad. Sci. USA. 87, 6624–6628.

Grant, D. S., Tashiro, K.-l., Sequi-Real, B., Yamada, Y., Martin, G. R., and Kleinman, H. K. (1989). Two different laminin domains mediate the differentiation of human endothelial cells into capillary-like structures in vitro. Cell 58, 933–943.

Gross, J. L., Moscatelli, D., and Rifkin, D. B. (1983). Increased capillary endothelial cell protease activity in response to angiogenic stimuli in vitro. Proc. Natl. Acad. Sci. USA 80, 2623–2627.

Gupta, S. K., Hassel, T., and Singh, J. P. (1995). A potent inhibitor of endothelial cell proliferation is generated by proteolytic cleavage of the chemokine platelet factor 4. Proc. Natl. Acad. Sci. USA 92, 7799–7803.

Holmgren, L., O'Reilly, M. S., and Folkman, J. (1995). Dormancy of micrometastases: balanced proliferation and apoptosis in the presence of angiogenesis suppression. Nature Med. 1, 149–153.

Homandberg, G. A., Williams, J. E., Grant, D., B., S., and Eisenstein, R. (1985). Heparin-binding fragments of fibronectin are potent inhibitors of endothelial cell growth. Am. J. Path. 120, 327–332.

Hori, A., Sasada, R., Matsutani, E., Naito, K., Sakura, Y., Fujita, T., and Kozai, Y. (1991). Suppression of solid tumor growth by immunoneutralizing monoclonal antibody against human basic fibroblast growth factor. Cancer Res. 51, 6180–6184.

Kandel, J., Bossy-Wetzel, E., Radvany, F., Klagsbum, M., Folkman, J., and Hanahan, D. (1991). Neovascularization is associated with a switch to the export of bFGF in the multistep development of fibrosarcoma. Cell 66, 1095–1104.

Kim, K. J., Li, B., Winer, J., Armanini, M., Gillett, N., Phillips, H. S., and Ferrara, N. (1993). Inhibition of vascular endothelial growth factor-induced angiogenesis suppresses tumor growth in vivo. Nature 362, 841–844.

Maione, T. E., Gray, G. S., Petro, J., Hunt, A. J., Donner, A. L., Bauer, S. I., Carson, H. F., and Sharpe, R. J. (1990). Inhibition of angiogenesis by recombinant human platelet factor-4 and related peptides. Science 247, 77–79.

Millauer, B., Shawver, L. K., Plate, K. H., Risau, W., and Ullrich, A. (1994). Glioblastoma growth inhibited in vivo by a dominant-negative Flk-1 mutant. Nature 367, 576–579.

Muragaki, Y., Timmons, S., Griffith, C. M., Oh, S. P., Fadel, B., Quertemmous, T., and Olsen, B.-R. (1995). Mouse col18a1 is expressed in a tissue-specific manner as three alternative variants and is localized in basement membrane zones. Proc. Natl. Acad. Sci. USA 92, 8763–8767.

Nelson, J., Allen, W. E., Scott, W. N., Bailie, J. R., Walker, B., and McFerran, N. V. (1995). Murine epidermal growth factor (EGF) fragment (33–42) inhibits both EGF- and laminin-dependent endothelial cell motility and angiogenesis. Cancer Res. 55, 3772–3776.

Nguyen, M., Shing, Y., and Folkman, J. (1994). Quantitation of angiogenesis and antiangiogenesis in the chick embryo chorioallantoic membrane. Microvascular Res. 47, 31–40.

O'Reilly, M. S., Holmgren, L., Chen, C. C., and Folkman, J. (1996). Angiostatin protein induces and sustains dormancy of human primary tumors in mice. Nature Med. 2, 689–692.

O'Reilly, M. S., Holmgren, L., Shing, Y., Chen, C., Rosenthal, R. A., Moses, M., Lane, W. S., Cao, Y., Sage, E. H., and Folkman, J. (1994). Angiostatin protein: A novel angiogenesis inhibitor that mediates the suppression of metastases by a Lewis lung carcinoma. Cell 79, 315–328.

Obeso, J., Weber, J., and Auerbach. R. (1990). A hemangioendothelioma-derived cell line: its use as a model for the study of endothelial cell biology. Lab. Invest. 63, 259–269.

Oh, S. K., Kamagata, Y., Muragaki, Y., Timmons, S., Ooshima, A., and Olsen, B. R. (1994). Isolation and sequencing of cDNAs for proteins with multiple domains of GlyXaa-Yaa repeats identify a distinct family of collagenous proteins. Proc. Natl. Acad. Sci. USA 91, 4229–4233.

Parangi, S., O'Reilly, M., Christofori, G., Holmgren, L., Grosfeld, J., Folkman, J., and Hanahan, D. (1996). Antiangiogenic therapy of transgenic mice impairs de novo tumor growth. Proc. Natl. Acad. Sci. USA 93, 2002–2007.

Rastinejad, F., Polyerini, P. J., and Bouck, N. P. (1989). Regulation of the activity of a new inhibitor of angiogenesis by a cancer suppressor gene. Cell 56, 345–355.

Rehn, M., and Pihlajaniemi, T. (1994). a1(XVIII), a collagen chain with frequent interruptions in the collagenous sequence, a distinct tissue distribution, and homology with type XV collagen. Proc. Natl. Acad. Sci. USA 91, 4234–4238.

Rehn, M., and Pihlajaniemi, T. (1995). Identification of three N-terminal ends of type XVIII collagen chains and tissue-specific differences in the expression of the corresponding transcripts. J. Biol. Chem. 270, 4705–4711.

Sage, E. H., Bassuk, J. A., Vost, J. C., Folkman. M. J., and Lane, T. F. (1995). Inhibition of endothelial cell proliferation by SPARC is mediated through a Ca (2+)-binding EF-hand sequence. J. Cell Biochem. 57, 127–140.

Sakamato, N., Iwahana, M., Tanaka, N. G., and Osaka, 8. (1991). Inhibition of angiogenesis and tumor growth by a synthetic laminin peptide, CDPGYIGSR—$NH_2$. Cancer Res. 51, 903–906.

Strieter, R. M., Kunkel, S. L., Arenberg, D. A., Burdick, M. D., and Polyerini, P. J. (1995). Human interferon-inducible protein 10 (IP-10), a member of the C-X-C chemokine family, is an inhibitor of angiogenesis. Biochem. Biophys. Res. Comm. 210, 51–57.

Studier, W. F., Rosenberg, A. H., Dunn, J. J., and Dudendorf, J. W. (1990). Use of T7 RNA polymerase to direct expression of cloned genes. Methods Enzymol. 85, 60–89.

Teicher, B. A., Holden, S. A., Ara, G., Sotomayor, E. A., and Dong, H. Z. (1994). Potentiation of cytotoxic cancer therapies by TNP-470 alone and with other antiangiogenic agents. Int. J. Cancer 57, 1–6.

Tolsma, S. S., Volpert, O. V., Good, D. J., Frazier, W. A., Polyerini, P. J., and Bouck, N. (1993). Peptides derived from two separate domains of the matrix protein thrombospondin-1 have antiangiogenic activity. J. Cell Biol. 122, 497–511.

Voest, E. E., Kenyon, B. M., O'Reilly, M. S., Truitt, G., D'Amato, R. J., and Folkman, J. (1995). Inhibition of angiogenesis in vivo by interleukin 12. J. Natl. Cancer Inst. 87, 581–586.

What is claimed is:

1. An isolated antibody specific for endostatin protein, wherein the protein is an antiangiogenic fragment of a C-terminal NC1 region of a collagen XVIII or XV protein.

2. The isolated antibody of claim 1, wherein the collagen protein is collagen type XVIII protein.

3. The isolated antibody of claim 1, wherein the collagen protein is collagen type XV protein.

4. The isolated antibody of claim 1, wherein the fragment is produced recombinantly.

5. The isolated antibody of claim 1, wherein the fragment is naturally occurring.

6. The isolated antibody of claim 1, wherein the fragment is from a human.

7. The isolated antibody of claim 1, wherein the fragment inhibits angiogenesis in vivo.

8. The isolated antibody of claim 1, wherein the fragment inhibits angiogenesis in vitro.

9. The isolated antibody of claim 1, wherein the fragment comprises an amino acid sequence as shown in SEQ ID NO:1.

10. The isolated antibody of claim 1, wherein the antibody is monoclonal.

11. A hybridoma producing the monoclonal antibody of claim 10.

12. The isolated antibody of claim 1, wherein the fragment comprises an amino acid sequence as shown in SEQ ID N:2.

13. An isolated antibody that inhibits the binding of the antibody of claim 1.

14. A kit for the detection of a fragment of an NC1 region, comprising the antibody of claim 1.

15. An isolated antibody specific for a fragment of an NC1 region of a collagen XVIII or XV protein, wherein the fragment has a molecular weight of approximately 18 kDa as determined by non-reduced gel electrophoresis, and approximately 20 kDa as determined by reduced gel electrophoresis, wherein the fragment binds to a heparin affinity column and does not bind to a lysine affinity column, and wherein the fragment inhibits angiogenesis.

16. The isolated antibody of claim 15, wherein the collagen protein is collagen type XVIII protein.

17. The isolated antibody of claim 15, wherein the collagen protein is collagen type XV protein.

18. The isolated antibody of claim 15, wherein the fragment is produced recombinantly.

19. The isolated antibody of claim 15, wherein the fragment is naturally occurring.

20. The isolated antibody of claim 15, wherein the fragment is from a human.

21. The isolated antibody of claim 15, wherein the fragment inhibits angiogenesis in vivo.

22. The isolated antibody of claim 15, wherein the fragment inhibits angiogenesis in vitro.

23. The isolated antibody of claim 15, wherein the fragment comprises an amino acid sequence as shown in SEQ ID NO:1.

24. The isolated antibody of claim 15, wherein the antibody is monoclonal.

25. A hybridoma producing the monoclonal antibody of claim 24.

26. The isolated antibody of claim 15, wherein the fragment comprises an amino acid sequence as shown in SEQ ID NO:2.

27. An isolated antibody that inhibits the binding of the antibody of claim 15.

28. A kit for the detection of a fragment of an NC1 region, comprising the antibody of claim 15.

* * * * *

SEQUENCE LISTING

<160> NUMBER OF SEQ ID NOS: 3

<210> SEQ ID NO 1
<211> LENGTH: 20
<212> TYPE: PRT
<213> ORGANISM: Murinae gen. sp.

<400> SEQUENCE: 1

```
His Thr His Gln Asp Phe Gln Pro Val Leu His Leu Val Ala Leu Asn
1               5                   10                  15

Thr Pro Leu Ser
            20
```

<210> SEQ ID NO 2
<211> LENGTH: 26
<212> TYPE: PRT
<213> ORGANISM: Murinae gen. sp.

<400> SEQUENCE: 2

```
Cys Lys Asp Glu Leu Leu Phe Pro Ser Trp Glu Ala Leu Phe Ser Gly
1               5                   10                  15

Ser Glu Gly Pro Leu Lys Pro Gly Ala Arg
            20                  25
```

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide

<400> SEQUENCE: 3

```
Met Ala Arg Arg Ala Ser Val Gly Thr Asp
1               5                   10
```